United States Patent
Sala et al.

(10) Patent No.: US 8,524,812 B2
(45) Date of Patent: Sep. 3, 2013

(54) STABILIZERS

(75) Inventors: Massimiliano Sala, Castelnuovo Rangone (IT); Giulia Cocco, Savigno (IT); Anna Bassi, Ludwigshafen (DE); Michael Roth, Lautertal (DE); Kai-Uwe Schöning, Oberwil (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/146,942

(22) PCT Filed: Jan. 26, 2010
(Under 37 CFR 1.47)

(86) PCT No.: PCT/EP2010/050875
§ 371 (c)(1),
(2), (4) Date: Nov. 18, 2011

(87) PCT Pub. No.: WO2010/089230
PCT Pub. Date: Aug. 12, 2010

(65) Prior Publication Data
US 2012/0108711 A1    May 3, 2012

(30) Foreign Application Priority Data
Feb. 4, 2009   (EP) .................................... 09152043

(51) Int. Cl.
C08K 5/3492   (2006.01)
C07D 403/14   (2006.01)

(52) U.S. Cl.
USPC .............. 524/100; 524/96; 544/198; 544/209

(58) Field of Classification Search
USPC ............................ 524/96, 100; 544/198, 209
See application file for complete search history.

(56) References Cited

U.S. PATENT DOCUMENTS

| | | | |
|---|---|---|---|
| 4,442,250 A | | 4/1984 | Cantatore |
| 5,004,759 A | * | 4/1991 | Mutterer et al. ................ 524/89 |
| 5,844,026 A | | 12/1998 | Galbo |
| 5,847,132 A | * | 12/1998 | Borzatta et al. .............. 544/198 |
| 6,046,304 A | * | 4/2000 | Borzatta et al. .............. 528/423 |
| 6,465,645 B1 | | 10/2002 | Wood |
| 7,122,663 B2 | | 10/2006 | Zedda et al. |
| 2004/0063932 A1 | | 4/2004 | Zedda et al. |

FOREIGN PATENT DOCUMENTS

WO     02058844 A    8/2002

OTHER PUBLICATIONS

Chimassorb (TM) 966, Internet Citation (is cumulative to U.S. Patents 7,122,663 and U.S. 4,442,250).

* cited by examiner

*Primary Examiner* — Kriellion Sanders
(74) *Attorney, Agent, or Firm* — Tyler A. Stevenson

(57) ABSTRACT

N-substituted Macrocyclic Triazine-HALS Stabilizers.

11 Claims, No Drawings

STABILIZERS

The present invention relates to a composition of cyclic sterically hindered amine stabilizers with 4 pending 2,2,6,6-tetramethyl-piperidine groups. These groups are substituted at the nitrogen atom by 2 to 4 substituents in a specific ratio. Further aspects of the invention are the individual components, an agricultural polymeric article containing such a composition, a process for stabilizing a polymeric article and the use of the composition as stabilizer and flame retardant.

Sterically hindered amines (HAS) are known to be efficient polymer stabilizers against the harmful effect of light and heat, in particular for polyolefins.

However, primary or secondary not sterically hindered amines, may be present as reaction by products in some commercially available HAS. These by products can negatively influence the stabilizing efficiency.

Chimassorb 966 is a commercial sterically hindered amine stabilizer, which does not have this problem because primary or secondary not sterically hindered amines are principally not present in its macrocyclic structure.

However, the melting point of Chimassorb 966 is higher than 290° C. Usually the processing temperature of polymers, in particular polyolefins is below 290° C. For this reason Chimassorb 966 when used as polyolefin stabilizer will not or not completely melt during processing. As a consequence, films stabilized with Chimassorb 966 could be affected by a high number of gels due to unmelted spots. For this reason, the use of Chimassorb 966 as stabilizer in film applications where high numbers of gels are undesired causes problems.

It has now, surprisingly, been found that, if the hindered nitrogen atoms in the rings of the 2,2,6,6-tetramethylpiperidine heterocyclic moieties are substituted in part or in an exhaustive way with specific substituents, the melting point can be substantially reduced below 250° C., the excellent stabilizing efficiency remains. Thus substituted compounds can now be used advantageously in all thin film applications, for example, of polyolefins.

One aspect of the invention is a composition comprising (a) a natural or synthetic polymer subject to degradation induced by light, heat or oxidation, and (b) 0.001 to 10% by weight, relative to the weight of the natural or synthetic polymer of a product mixture containing components b-I, b-II, b-III and b-IV;

component b-I being a compound of formula (I) with a degree of substitution of 1 in an amount of from 0 to 30 parts by weight, component b-II being a compound of formula (I) with a degree of substitution of 2 in an amount of from 0 to 50 parts by weight, component b-III being a compound of formula (I) with a degree of substitution of 3 in an amount of from 10 to 50 parts by weight and component b-IV being a compound of formula (I) with a degree of substitution of 4 in an amount of from 10 to 60 parts by weight, the sum of the parts of components bI to bIV being 100;

formula (I) being

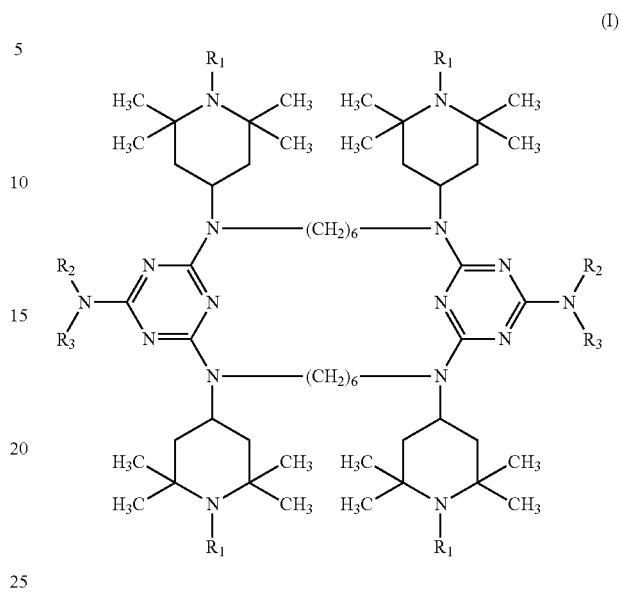

wherein the radicals $R_1$ are $C_4$-$C_{20}$alkyl, $C_4$-$C_{20}$alkoxy, $C_3$-$C_{12}$cycloalkoxy or a group of the formula

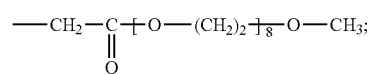

wherein for component b-I and b-II the radicals $R_1$ can additionally be hydrogen, oxygen or hydroxyl;

where degree of substitution denotes the number of substituents $R_1$ which are $C_4$-$C_{20}$alkyl, $C_4$-$C_{20}$alkoxy, $C_3$-$C_{12}$cycloalkoxy or a group of the formula

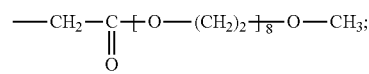

the radicals $R_2$ and $R_3$ are independently of one another hydrogen, $C_1$-$C_{12}$alkyl, $C_5$-$C_{12}$cycloalkyl unsubstituted or substituted by 1 to 3 $C_1$-$C_4$alkyl; phenyl unsubstituted or substituted by 1 to 3 radicals selected from —OH and $C_1$-$C_{10}$alkyl; $C_7$-$C_9$phenylalkyl unsubstituted or substituted on the phenyl by 1 to 3 radicals selected from —OH and $C_1$-$C_{10}$alkyl; or a group of the formula (I-1)

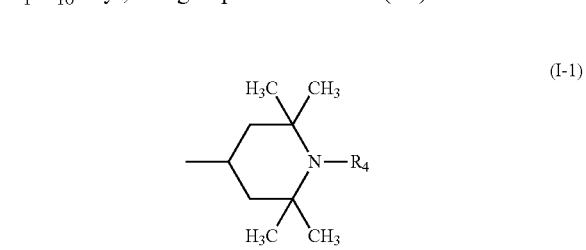

wherein $R_4$ is hydrogen, $C_4$-$C_{20}$alkyl, $C_4$-$C_{20}$alkoxy, $C_3$-$C_{12}$cycloalkoxy or a group of the formula

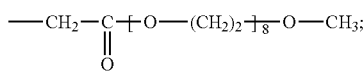

or
the radicals $R_2$ and $R_3$, together with the nitrogen they are attached to, form a morpholino group.

Under degree of substitution there is understood the number of substituents $R_1$ which are $C_4$-$C_{20}$alkyl, $C_4$-$C_{20}$alkoxy, $C_3$-$C_{12}$cycloalkoxy or a group of the formula

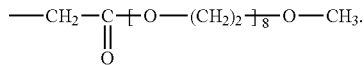

The degree of substitution can be from 2 to 4. Preferably it is from 2 to 3. For a degree of substitution of 2, several isomers are possible and are comprised.

Preferably the total amount of components b-I to b-IV is from 0.01 to 1% by weight, relative to the weight of the natural or synthetic polymer Preferably the amount of component b-I is from 5 to 25 parts, component b-II from 5 to 35 parts, component b-III from 10 to 45 parts and component b-IV from 10 to 45 parts.

Alkyl with up to 20 carbon atoms is, for example, methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl.

$C_1$-$C_{20}$alkoxy $G_{11}$ is, for example, methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$-$C_{12}$alkoxy, in particular heptoxy and octoxy, is preferred.

$C_3$-$C_{12}$cycloalkoxy is, for example, cyclopropoxy, cyclopentoxy, cyclohexoxy, cycloheptoxy, cyclooctoxy, cyclodecyloxy and cyclododecyloxy. $C_5$-$C_8$cycloalkoxy, in particular cyclopentoxy and cyclohexoxy, is preferred.

Any $C_5$-$C_{12}$cycloalkyl substituents are, in particular, cyclopentyl and cyclohexyl.

$C_7$-$C_9$phenylalkyl is preferably benzyl.

Suitable natural or synthetic polymers are given below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or III a of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is gene-rated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethyl-lene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(α-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethyllene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybuty-leneadipate/terephthalate, polytetramethyleneadipate/terephthalate, polybutylensuccinate/-adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homopolymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydrooxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.
19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

It is also possible that biodegradable polymers are used in the present invention. Examples for such polymers are given below.

Biodegradable polymers of either natural or synthetic origin include but are not limited to Polyethylensuccinate (Lunare SE (Nihon Shokubai)),
Polybutylensuccinate (Bionolle 1000 (Showa Highpolymer)),
Polybutylensuccinate/adipate (Bionolle 3000 (Showa Highpolymer))
Polybutylensuccinate/carbonate (lupec (Mitsubishi Gas Chemicals)),
Polybutylensuccinate/terephtalate (Biomax (Dupont), Ecoflex (BASF), EasterBio (Eastman Chemicals))
Polycaprolactone (CelGreen PH (Daicel Kagaku), Tone (UCC))
Poly(hydroxyalkanoates) (Nodax from Procter and Gamble or from Metabolix),
Poly 3-hydroxybutyrate (Biogreen (Mitsubishi Gas Chemicals))
Polylactic acid (NatureWorks (Cargill), LACEA (Mitsui Chemicals) Lacty (Shimadzu Seisakusho)),
Polyester amides
or blends of these materials with natural or modified starch, polysaccharides, lignin, wood flour, cellulose and chitin.

Preferred are synthetic polymers in particular thermoplastic polymers. Especially preferred are polyolefins as mentioned under items 1 to 3 above.

For example, in formula (I) the $R_1$ are $C_4$-$C_{12}$alkyl, $C_4$-$C_{12}$alkoxy, $C_5$-$C_6$cycloalkoxy.

For instance in formula (I) the group —$NR_2R_3$ is a group of formulae (II)

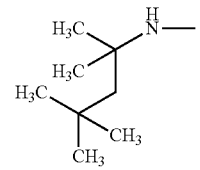

(III)

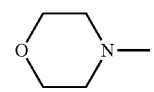

or (IV)

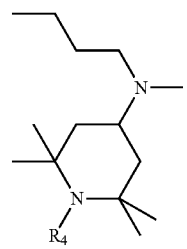

wherein $R_4$ has the meaning as given above.

Particularly preferred is when in formula (I) the group —$NR_2R_3$ is of formula (II)

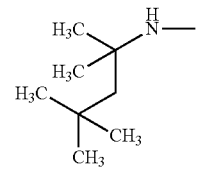

The compounds of formula (I) may be prepared from the corresponding amine precursors ($R_1$ is H) which are known and, for example, described in U.S. Pat. No. 4,442,250. When —$NR_2R_3$ is of formula (II), the amine precursor is a commercial product, Chimassorb® 966, sold by Ciba Inc.

When a part of the $R_1$ is oxygen (—O.) or hydroxyl (—OH) the oxidation may be carried out in analogy to the oxidation of 4-hydroxy-2,2,6,6-tetramethylpiperidine described in U.S. Pat. No. 5,654,434 with hydrogen peroxide. Another also suitable oxidation process is described in WO 00/40550 using peracetic acid.

The oxidation must not be carried out until all piperidine nitrogen atoms are oxidized. It can be stopped at many stages before, thus leading to a product mixture which contains NH, NOH and NO. moieties.

A further aspect of the invention is a compound of formula (Ia)

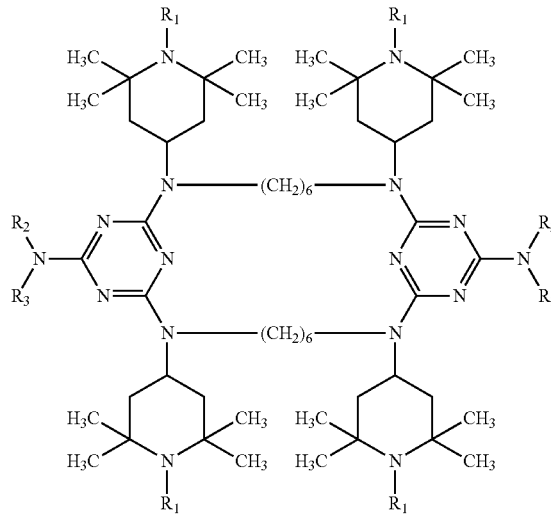

wherein in formula (Ia)
2, 3 or 4 of the radicals $R_1$ are $C_4$-$C_{20}$alkyl, $C_4$-$C_{20}$alkoxy, $C_3$-$C_{12}$cycloalkoxy or a group of the formula

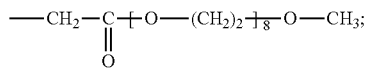

and the remaining radicals $R_1$ are hydrogen, oxygen or hydroxyl;

the radicals $R_2$ and $R_3$ in formulae (Ia) are independently of one another hydrogen, $C_1$-$C_{12}$alkyl, $C_5$-$C_{12}$cycloalkyl unsubstituted or substituted by 1 to 3 $C_1$-$C_4$alkyl; phenyl unsubstituted or substituted by 1 to 3 radicals selected from —OH and $C_1$-$C_{10}$alkyl; $C_7$-$C_9$phenylalkyl unsubstituted or substituted on the phenyl by 1 to 3 radicals selected from —OH and $C_1$-$C_{10}$alkyl; or a group of the formula (I-1)

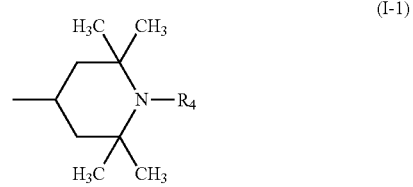

wherein $R_4$ is hydrogen, $C_4$-$C_{20}$alkyl, $C_4$-$C_{20}$alkoxy, $C_3$-$C_{12}$cycloalkoxy or a group of the formula

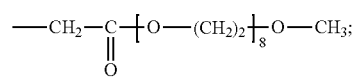

or the radicals $R_2$ and $R_3$, together with the nitrogen they are attached to, form a morpholino group.

Suitable individual compounds according to the invention are given below:

Compound (1)

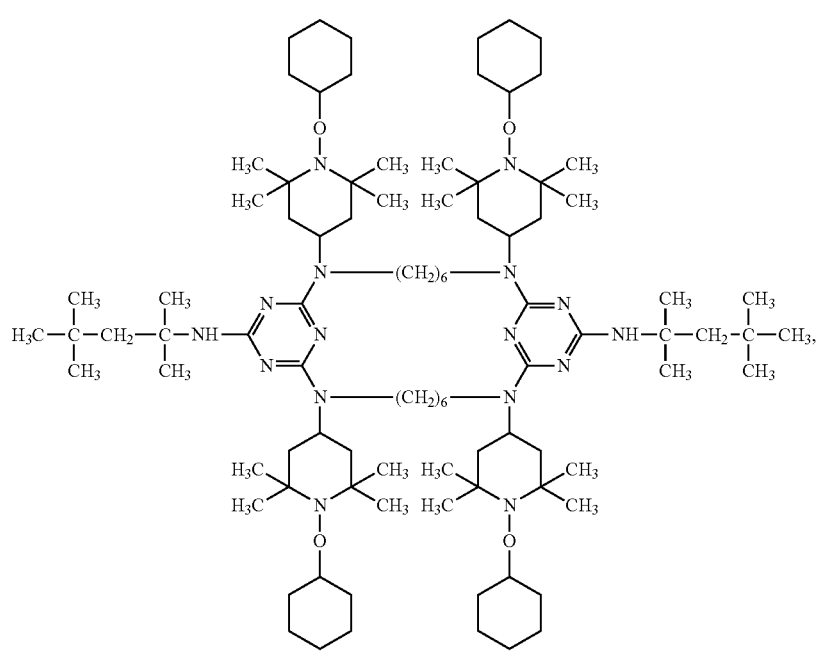

Compound (2)
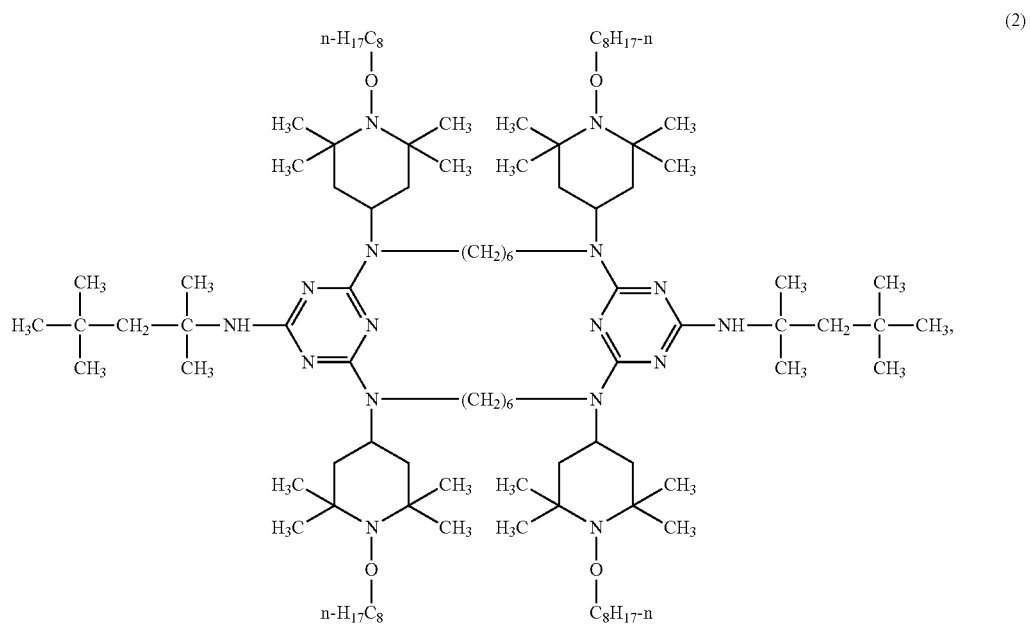
Compound (3)
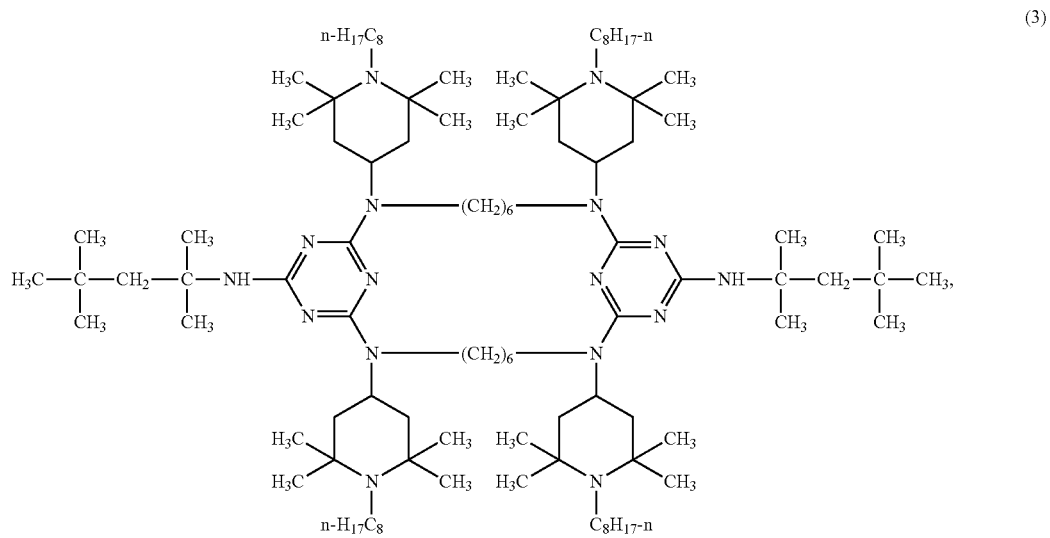

Compound (4)
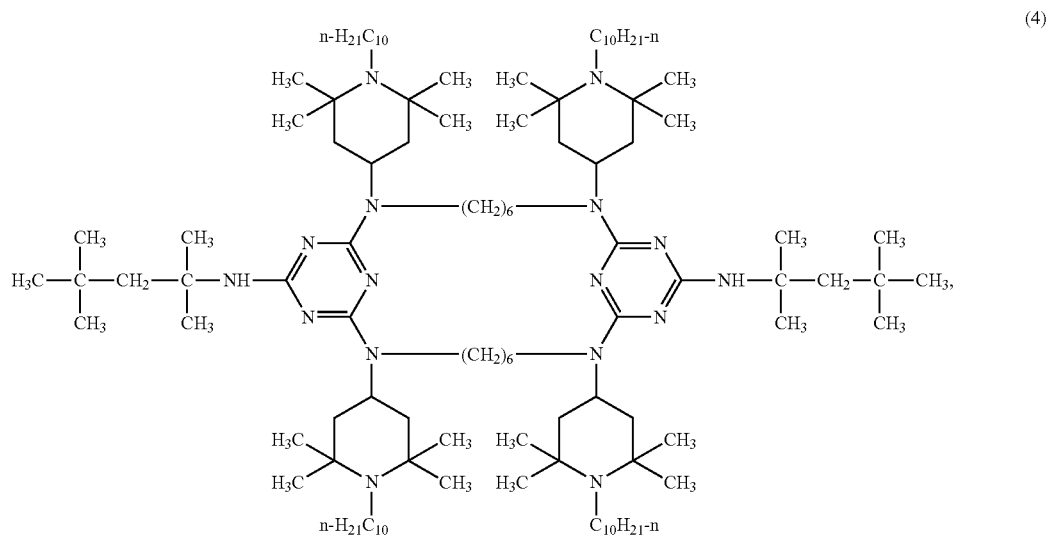
(4)
Compound (5)
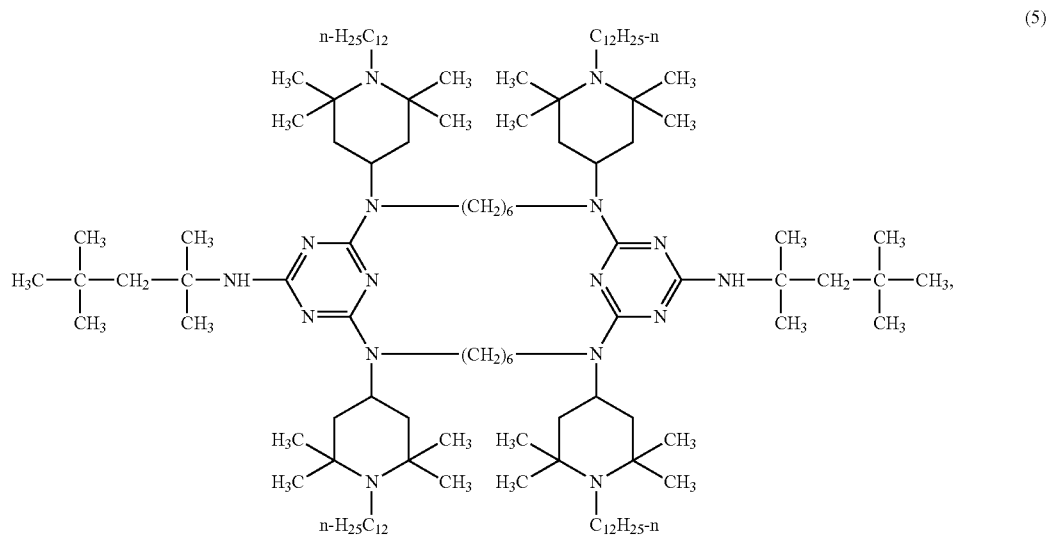
(5)

Compound (6)
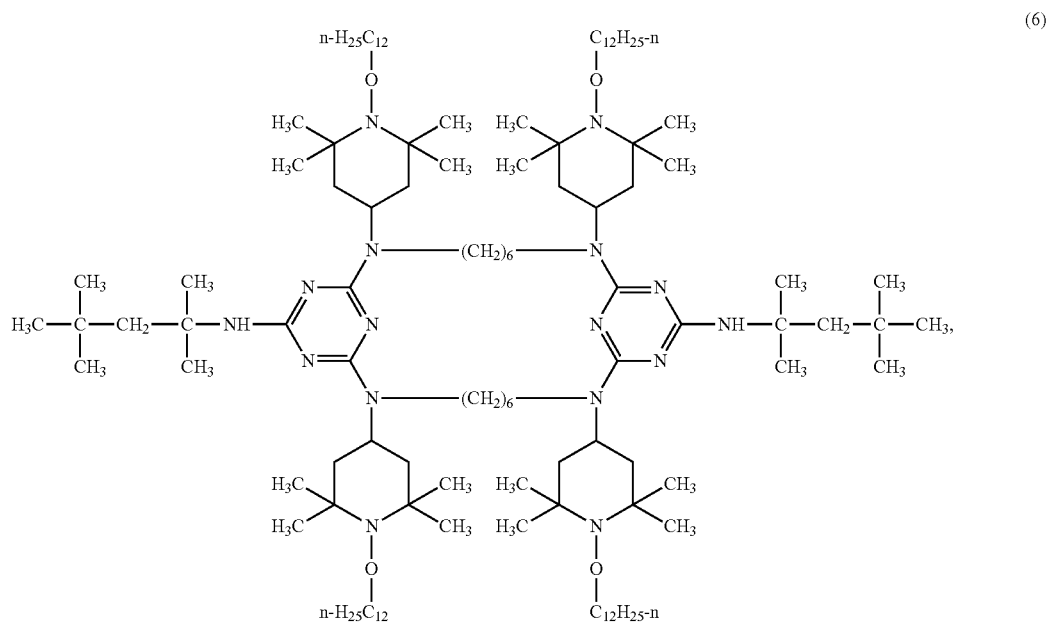
Compound (7)
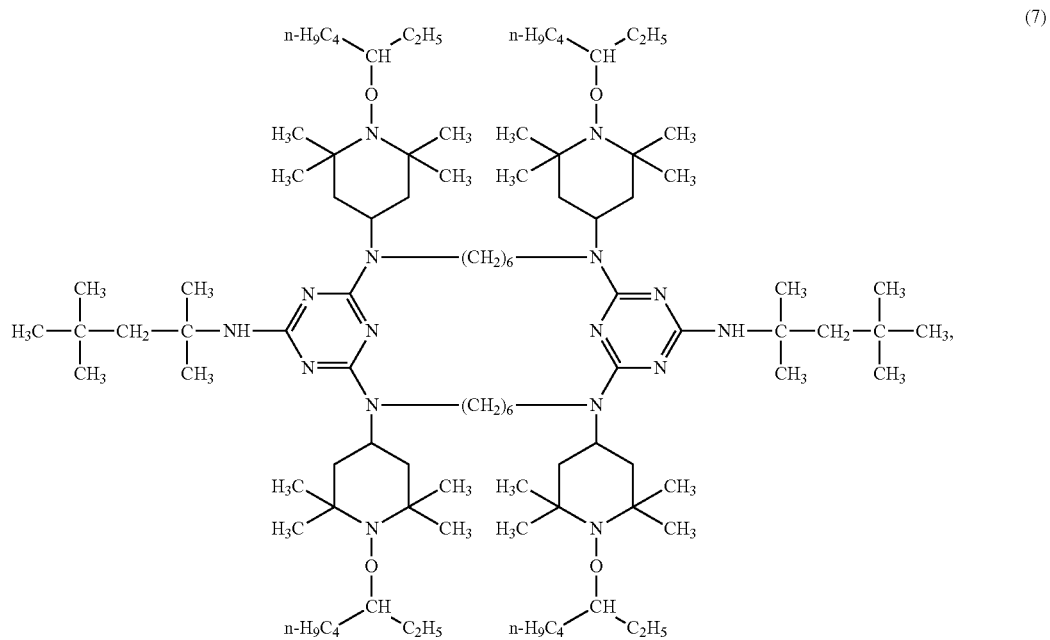

Compound (8)
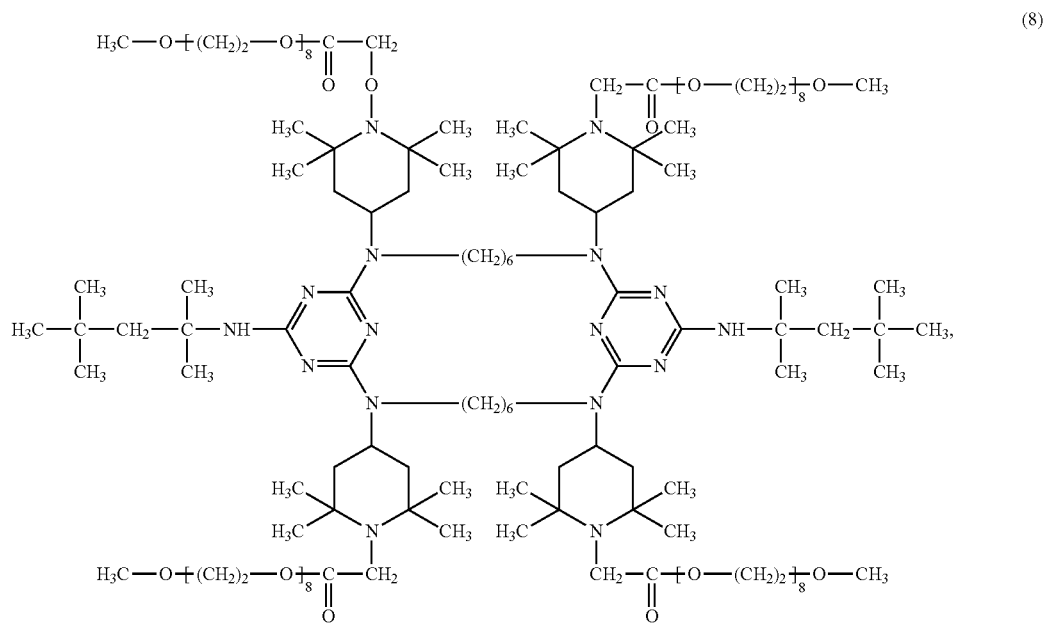
Compound (9)
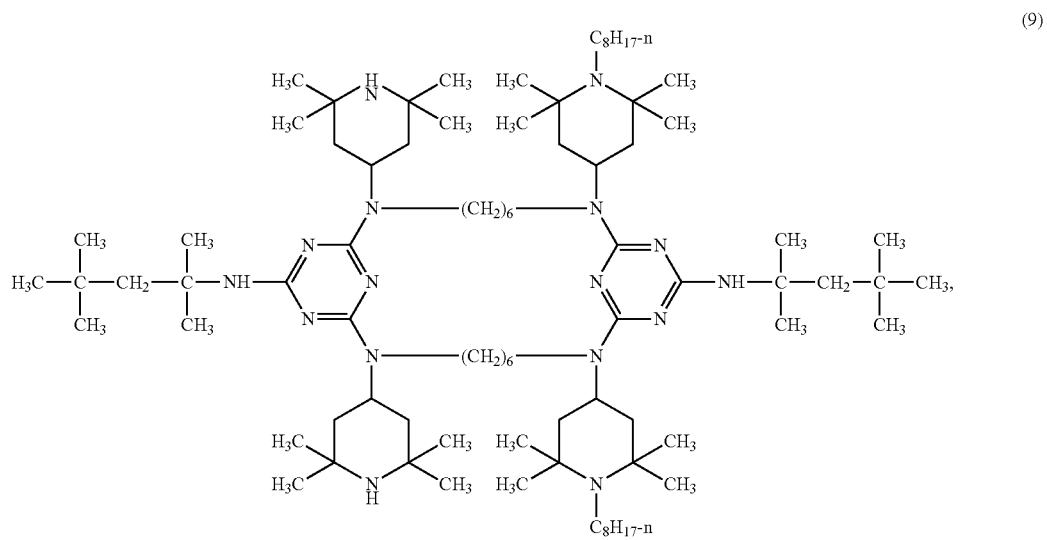

Compound (10)
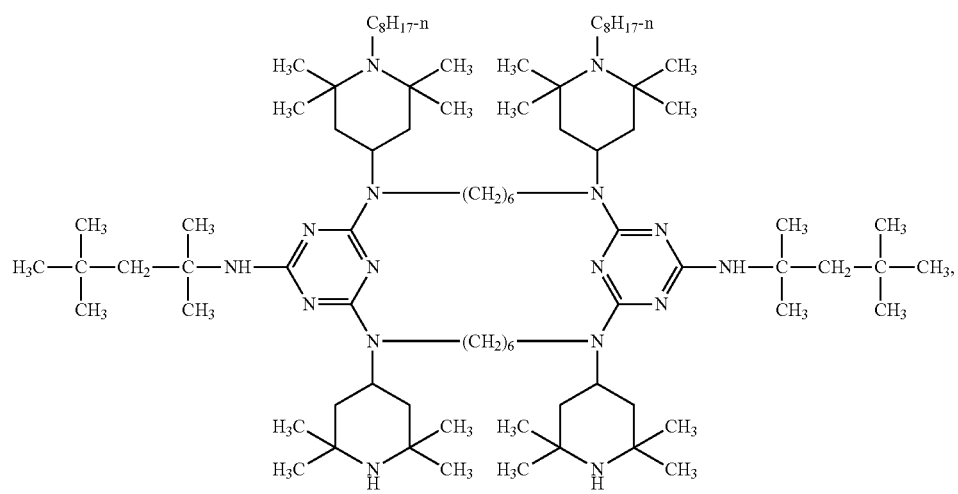
Compound (11)
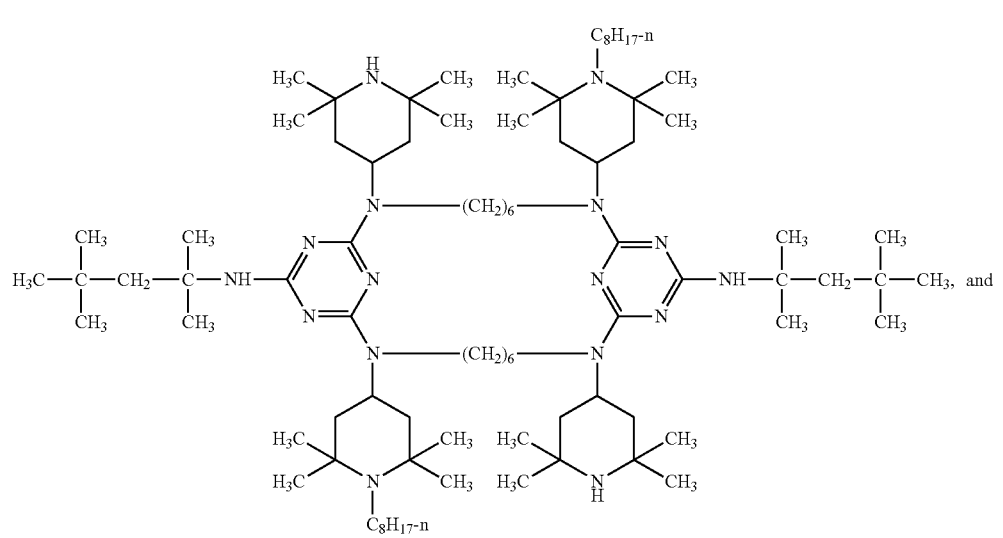
Compound (12)
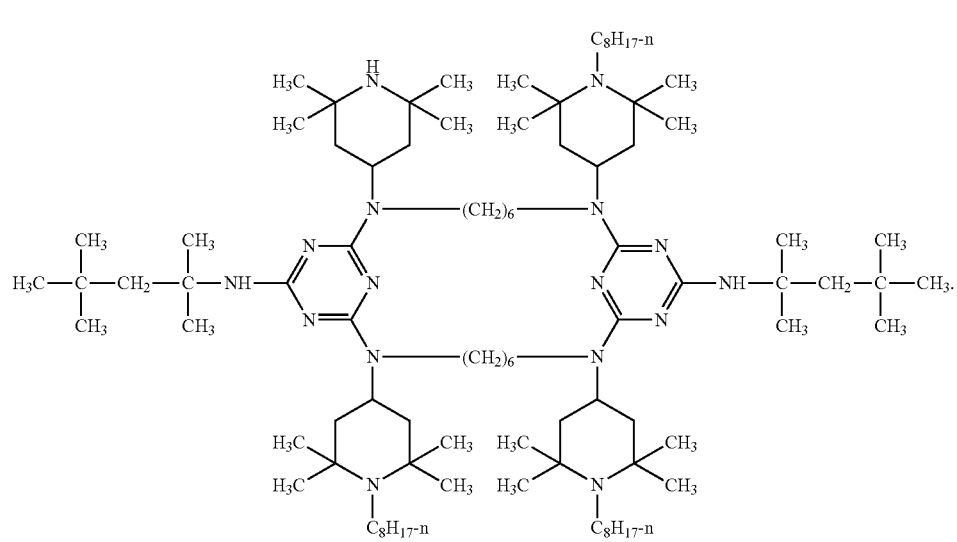

Further aspects of the invention are a stabilizer composition comprising a product mixture containing components b-I, b-II, b-III and b-IV;
component b-I being a compound of formula (I) with a degree of substitution of 1 in an amount of from 0 to 30 parts by weight,
component b-II being a compound of formula (I) with a degree of substitution of 2 in an amount of from 0 to 50 parts by weight,
component b-III being a compound of formula (I) with a degree of substitution of 3 in an amount of from 10 to 50 parts by weight and
component b-IV being a compound of formula (I) with a degree of substitution of 4 in an amount of from 10 to 60 parts by weight, the sum of the parts of components bI to bIV being 100;
formula (I) being

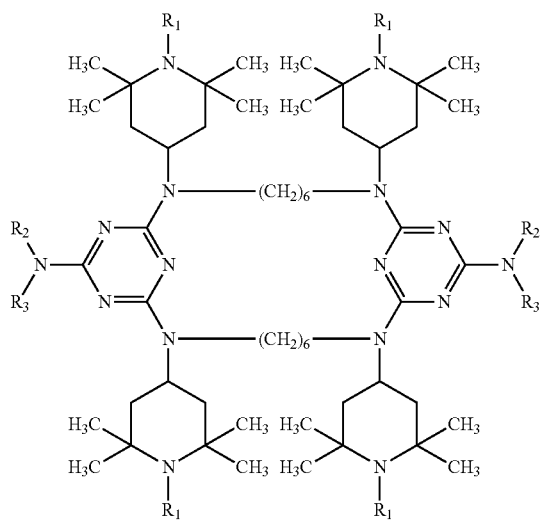

wherein
the radicals $R_1$ are $C_4$-$C_{20}$alkyl, $C_4$-$C_{20}$alkoxy, $C_3$-$C_{12}$cycloalkoxy or a group of the formula

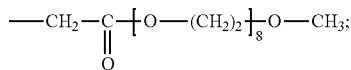

wherein for component b-I and b-II the radicals $R_1$ can additionally be hydrogen, oxygen or hydroxyl;
where degree of substitution denotes the number of substituents $R_1$ which are $C_4$-$C_{20}$alkyl, $C_4$-$C_{20}$alkoxy, $C_3$-$C_{12}$cycloalkoxy or a group of the formula

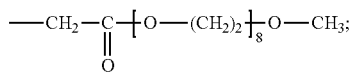

the radicals $R_2$ and $R_3$ are independently of one another hydrogen, $C_1$-$C_{12}$alkyl, $C_5$-$C_{12}$cycloalkyl unsubstituted or substituted by 1 to 3 $C_1$-$C_4$alkyl; phenyl unsubstituted or substituted by 1 to 3 radicals selected from —OH and $C_1$-$C_{10}$alkyl; $C_7$-$C_9$phenylalkyl unsubstituted or substituted on the phenyl by 1 to 3 radicals selected from —OH and $C_1$-$C_{10}$alkyl; or a group of the formula (I-1)

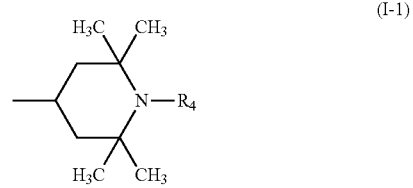

wherein $R_4$ is hydrogen, $C_4$-$C_{20}$alkyl, $C_4$-$C_{20}$alkoxy, $C_3$-$C_{12}$cycloalkoxy or a group of the formula

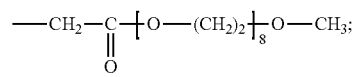

or
the radicals $R_2$ and $R_3$, together with the nitrogen they are attached to, form a morpholino group; and
a process for the stabilization of a natural or synthetic polymer subject to degradation induced by light, heat or oxidation comprising incorporating into said polymer
0.001 to 10% by weight, relative to the weight of the natural or synthetic polymer of a composition as described above.

The additives of the invention and optional further components may be added to the polymer material individually or mixed with one another. If desired, the individual components can be mixed with one another before incorporation into the polymer for example by dry blending, compaction or in the melt.

The incorporation of the additives of the invention and optional further components into the polymer is carried out by known methods such as dry blending in the form of a powder, or wet mixing in the form of solutions, dispersions or suspensions for example in an inert solvent, water or oil. The additives of the invention and optional further additives may be incorporated, for example, before or after molding or also by applying the dissolved or dispersed additve or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The addition of the additive or additive blend to the polymer can be carried out in all customary mixing machines in which the polymer is melted and mixed with the additives. Suitable machines are known to those skilled in the art. They are predominantly mixers, kneaders and extruders.

Particularly preferred processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion*, Vol. 1 Grundlagen, Editors F. Hensen, W. Knappe, H. Potente, 1989, pp. 3-7, ISBN: 3-446-14339-4 (Vol. 2 *Extrusionsanlagen* 1986, ISBN 3-446-14329-7).

For example, the screw length is 1-60 screw diameters, preferably 20-48 screw diameters. The rotational speed of the screw is preferably 1-800 rotations per minute (rpm), very particularly preferably 25-400 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

The additives of the invention and optional further additives can also be added to the polymer in the form of a masterbatch ("concentrate") which contains the components in a concentration of, for example, about 1% to about 40% and preferably 2% to about 20% by weight incorporated in a polymer. The polymer must not be necessarily of identical structure than the polymer where the additives are added finally. In such operations, the polymer can be used in the form of powder, granules, solutions, suspensions or in the form of latices.

Suitable furthers additives are the following.
1. Antioxidants
1.1. Alkylated Monophenols
1.2. Alkylthiomethylphenols
1.3. Hydroquinones and alkylated hydroquinones
1.4. Tocopherols
1.5. Hydroxylated Thiodiphenyl Ethers
1.6. Alkylidenebisphenols
1.7. O-, N- and S-benzyl compounds
1.8. Hydroxybenzylated Malonates
1.9. Aromatic hydroxybenzyl compounds
1.10. Triazine Compounds
1.11. Benzylphosphonates
1.12. Acylaminophenols
1.13. Esters of β-(3,5-di-tert-butyl-4-hydroxyphenyl)propionic acid with mono- or polyhydric alcohols
1.14. Esters of β-(5-tert-butyl-4-hydroxy-3-methylphenyl) propionic acid with mono- or polyhydric alcohols
1.15. Esters of β-(3,5-dicyclohexyl-4-hydroxyphenyl)propionic acid with mono- or polyhydric alcohols
1.16. Esters of 3,5-di-tert-butyl-4-hydroxyphenyl acetic acid with mono- or polyhydric alcohols
1.17. Amides of β-(3,5-di-tert-butyl-4-hydroxyphenyl)propionic acid
1.18. Ascorbic acid (vitamin C)
1.19. Aminic Antioxidants
2. UV absorbers and light stabilizers
2.1. 2-(2'-Hydroxyphenyl)benzotriazoles
2.2. 2-Hydroxybenzophenones
2.3. Esters of substituted and unsubstituted benzoic acids
2.4. Acrylates
2.5. Nickel compounds
2.6. Other sterically hindered amines
2.7. Oxamides
2.8. 2-(2-Hydroxyphenyl)-1,3,5-triazines
3. Metal deactivators
4. Phosphites and phosphonites
5. Hydroxylamines
6. Nitrones
7. Thiosynergists
8. Peroxide scavengers
9. Polyamide stabilizers
10. Basic co-stabilizers
11. Nucleating agents
12. Fillers and reinforcing agents
13. Other additives, for example plasticisers, lubricants, emulsifiers, pigments, rheology additives, catalysts, flow-control agents, optical brighteners, flameproofing agents, antistatic agents and blowing agents.
14. Benzofuranones and indolinones Examples from each of the above groups are described in further detail in U.S. Pat. No. 6,878,761.

The final product can be any type of plastic product, which needs stabilization in natural sunlight and/or humidity at low, ambient or elevated temperature. For example, the polymer component may be used to manufacture plastic films, sheets, bags, bottles, styrofoam cups, plates, utensils, blister packages, boxes, package wrappings, plastic fibers, tapes, agricultural articles such as twine agricultural films, mulch films, small tunnel films, banana bags, direct covers, nonwoven, pots for agricultural use, goetextiles, landfill covers, industrial covers, waste covers, temporary scaffolding sheets, building films, silt fences, poultry curtains, films for building temporary shelter constructions, disposable diapers, disposable garments, and the like. The articles may be manufactured by any process available to those of ordinary skill in the art including, but not limited to, extrusion, extrusion blowing, film casting, film blowing, calendering, injection molding, blow molding, compression molding, thermoforming, spinning, blow extrusion and rotational casting.

A preferred article is an agricultural article made of (a) a natural or synthetic polymer subject to degradation induced by light, heat or oxidation, and (b) 0.001 to 10% by weight, relative to the weight of the natural or synthetic polymer of a product mixture containing components b-I, b-II, b-III and b-IV;

component b-I being a compound of formula (I) with a degree of substitution of 1 in an amount of from 0 to 30 parts by weight, component b-II being a compound of formula (I) with a degree of substitution of 2 in an amount of from 0 to 50 parts by weight, component b-III being a compound of formula (I) with a degree of substitution of 3 in an amount of from 10 to 50 parts by weight and component b-IV being a compound of formula (I) with a degree of substitution of 4 in an amount of from 10 to 60 parts by weight, the sum of the parts of components bI to bIV being 100;

formula (I) being

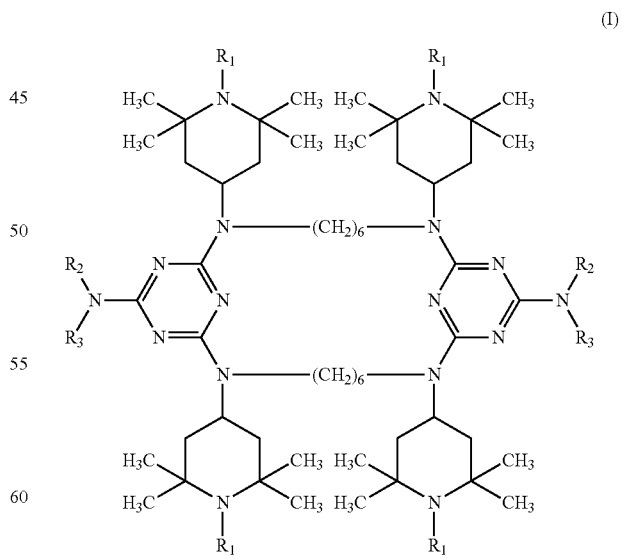

wherein the radicals $R_1$ are $C_4$-$C_{20}$alkyl, $C_4$-$C_{20}$alkoxy, $C_3$-$C_{12}$cycloalkoxy or a group of the formula

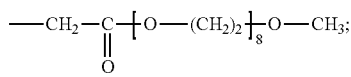

wherein for component b-I and b-II the radicals $R_1$ can additionally be hydrogen, oxygen or hydroxyl;

where degree of substitution denotes the number of substituents $R_1$ which are $C_4$-$C_{20}$alkyl, $C_4$-$C_{20}$alkoxy, $C_3$-$C_{12}$cycloalkoxy or a group of the formula

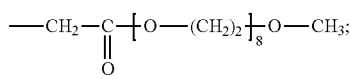

the radicals $R_2$ and $R_3$ are independently of one another hydrogen, $C_1$-$C_{12}$alkyl, $C_5$-$C_{12}$cycloalkyl unsubstituted or substituted by 1 to 3 $C_1$-$C_4$alkyl; phenyl unsubstituted or substituted by 1 to 3 radicals selected from —OH and $C_1$-$C_{10}$alkyl; $C_7$-$C_9$phenylalkyl unsubstituted or substituted on the phenyl by 1 to 3 radicals selected from —OH and $C_1$-$C_{10}$alkyl; or a group of the formula (I-1)

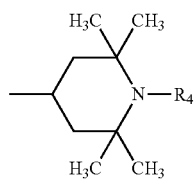
(I-1)

wherein $R_4$ is hydrogen, $C_4$-$C_{20}$alkyl, $C_4$-$C_{20}$alkoxy, $C_3$-$C_{12}$cycloalkoxy or a group of the formula

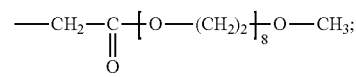

or the radicals $R_2$ and $R_3$, together with the nitrogen they are attached to, form a morpholino group.

In particular an agricultural article as described above wherein the compounds of formula (I) are of formula (Ic)

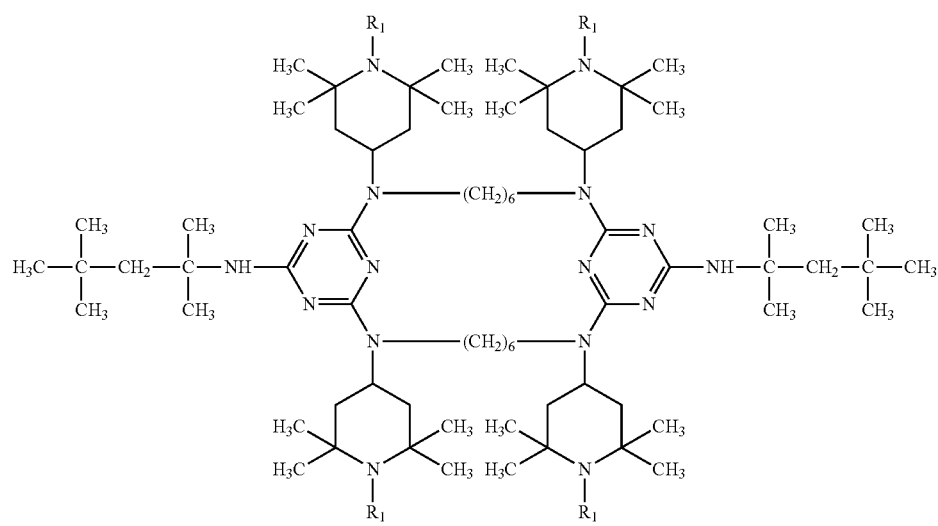

and the $R_1$ are as defined above.

Yet a further aspect of the invention is the use of a composition as defined above for the stabilization of a natural or synthetic polymer against degradation induced by light, heat or oxidation and the use of a said composition as a flame retardant for a natural or synthetic polymer.

Preferences and definitions given above apply equally for all aspects of the invention.

The following examples illustrate the invention.

Synthesis:

All chemicals are used as received and not purified prior to synthesis. All reactions are carried out in nitrogen atmosphere.

The following structure corresponds to the commercial Chimassorb 966 used as starting material for the synthesis of the below reported compounds:

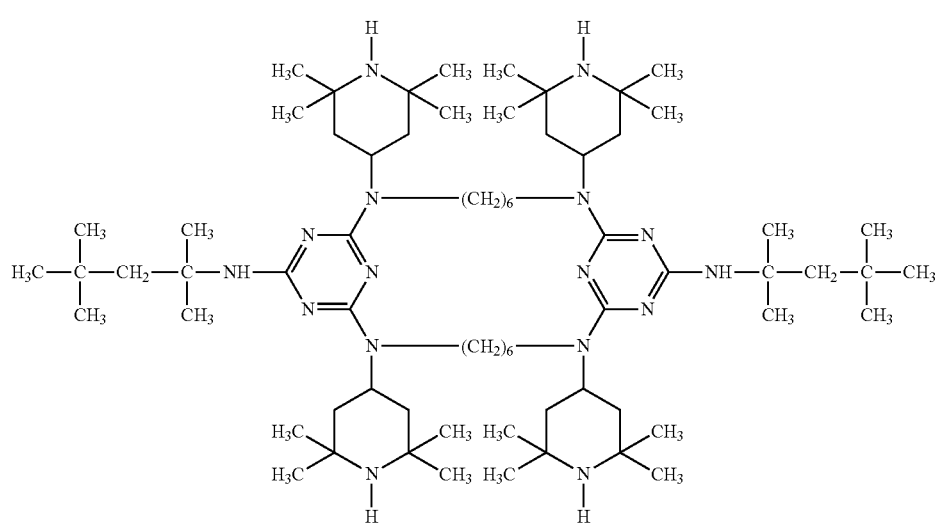
(Chimassorb 966)

In the structural formulae below all substituents at the nitrogen atom of the piperidine ring are outlined, although this is a mixture of mono-, di-, tri and tetra-substituted compounds. The respective amounts are given in the LCMS (liquid chromatography mass spectroscopy) data for each example.

EXAMPLE 1

Synthesis of Compound (101) Starting from Chimassorb 966

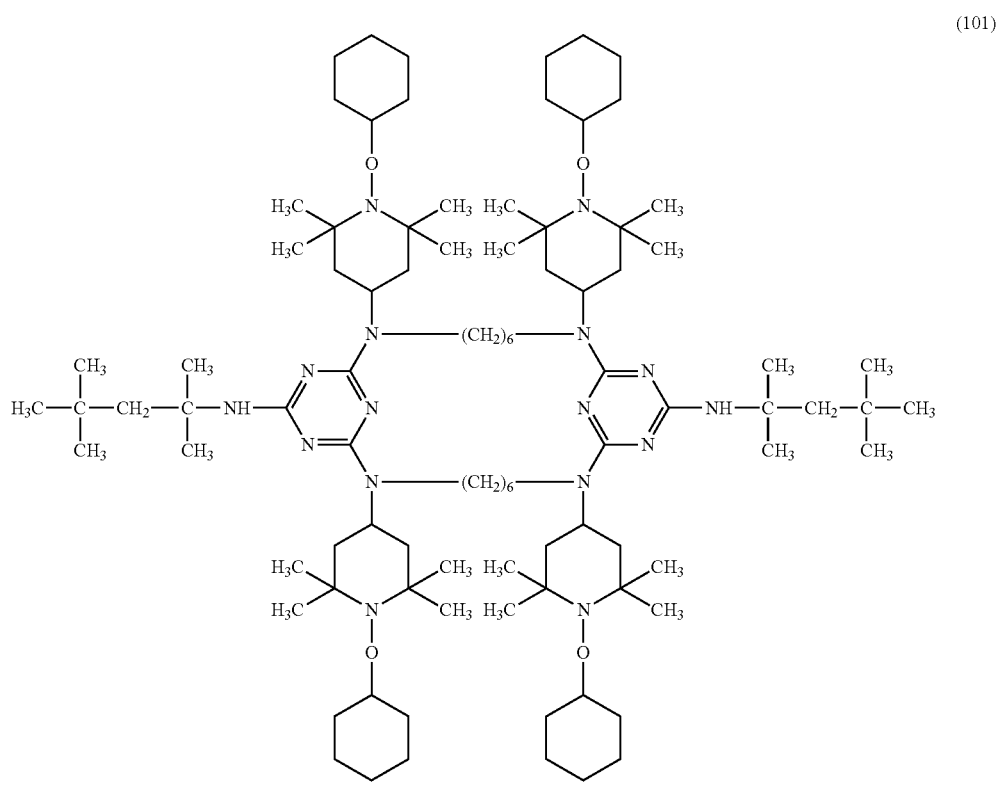
(101)

A four-necked round-bottom flask equipped with a mechanical stirrer, thermocouple, dropping funnel and condenser is successively charged with 50.0 g of Chimassorb 966, 500 ml of 1,2-dichlorobenzene, 2.5 g of Molybdenum (VI) oxide and 50.0 g of tert-butyl hydroperoxide 70% solution in water. The reaction mixture is then heated under stirring to azeotropic temperature removing the water in 4 hours by means of Marcusson apparatus. Thus, the reaction mixture is transferred in a 1 L autoclave and 200 ml of cyclohexane, 50.0 g of tert-butyl hydroperoxide 70% solution in water and 2.5 g of Molybdenum(VI) oxide are subsequently added. The reaction is then heated to 140° C. and left to react under stirring 4 hours. The mixture is then cooled to room temperature and filtered. 300 ml of water and 100.0 g of sodium sulfite are added to the crude filtered solution maintained under stirring. The organic phase is then separated and concentrated under vacuum. The crude beige residue is analyzed by $^1$H-NMR to reveal that the major part of the N—H groups of 2,2,6,6-tetramethylpiperidinic units of Chimassorb 966 are converted into the corresponding N-cyclohexyloxy thus forming compound (101).

Melting point: 215-235° C.

LCMS analysis provides the following product distribution in the final crude residue:

| Component | Approx. Amount (%) | Mass Found |
| --- | --- | --- |
| Chimassorb 966 (starting material) | <5% | 1196 not detected |
| Mono-substituted | <5% | 1296 not detected |
| Di-substituted | <5% | 1394 not detected |
| Tri-substituted | 15-30% | 1522 |
| Tetra-substituted | 40-60% | 1590 |

EXAMPLE 2

Synthesis of Compound (102) Starting from Chimassorb 966

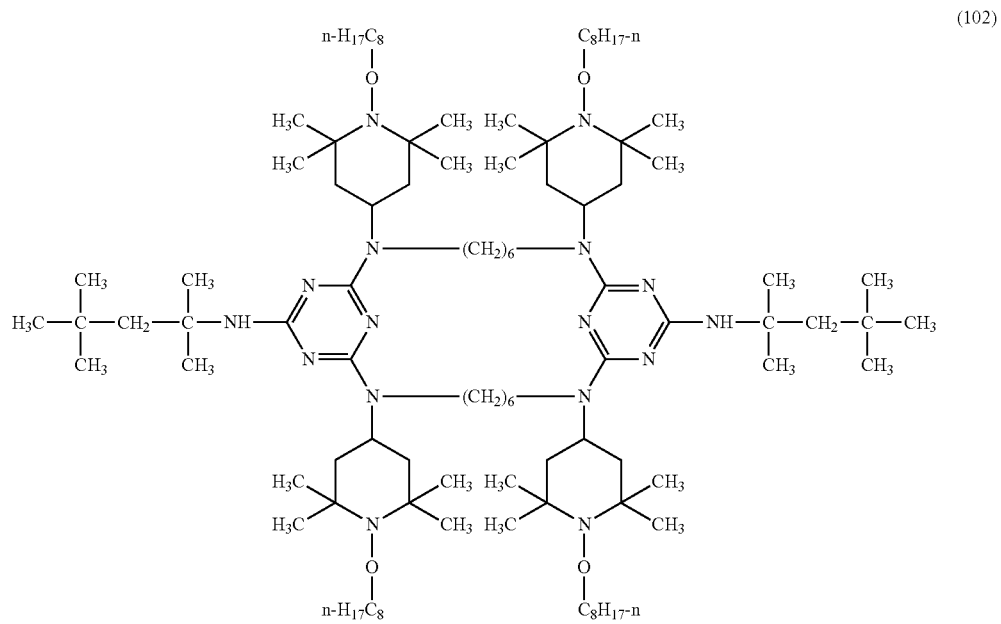

(102)

A four-necked round-bottom flask equipped with a mechanical stirrer, thermocouple, dropping funnel and condenser is successively charged with 50.0 g of Chimassorb 966, 500 ml of 1,2-dichlorobenzene, 2.5 g of Molybdenum (VI) oxide and 50.0 g of tert-butyl hydroperoxide 70% solution in water. The reaction mixture is then heated under stirring to azeotropic temperature removing the water in 4 hours by means of Marcusson apparatus. Thus, the reaction mixture is transferred in a 1 L autoclave and 200 ml of n-octane, 50.0 g of 70% solution of tert-butyl hydroperoxide in water and 2.5 g of Molybdenum(VI) oxide are subsequently added. The reaction is then heated to 140° C. and left to react under stirring 4 hours. The mixture is then cooled to room temperature and filtered. 300 ml of water and 100.0 g of sodium sulfite are added to the crude filtered solution maintained under stirring. The organic phase is then separated and concentrated under vacuum. The crude residue is analyzed by $^1$H-NMR to reveal that the major part of the N—H groups of 2,2,6,6-tetramethylpiperidinic units of Chimassorb 966 are converted into the corresponding N-octoxy thus forming compound (102).

Melting point: 112-135° C.

LCMS analysis provides the following product distribution in the final crude residue:

| Component | Approx. Amount (%) | Mass Found |
| --- | --- | --- |
| Chimassorb 966 (starting material) | <5% | 1196 not detected |

| Component | Approx. Amount (%) | Mass Found |
|---|---|---|
| Mono-substituted | 10-20% | 1416 |
| Di-substituted | 30-50% | 1514 |
| Tri-substituted | 10-20% | 1612 |
| Tetra-substituted | 10-20% | 1710 |

EXAMPLE 3

Synthesis of Compound (103) Starting from Chimassorb 966

A four-necked round-bottom flask equipped with a mechanical stirrer, thermocouple, dropping funnel and condenser is successively charged with 50.0 g of Chimassorb 996, 200 ml of 1,2-dichlorobenzene, 23.0 g of potassium carbonate, 1.0 g of potassium iodide and 56.0 g of 1-bromo octane. The mixture is maintained under stirring for 18 hours at reflux temperature. Thus, 200 ml of water are added to the cooled reaction solution and the organic phase is then separated and concentrated under reduced pressure. Then, the crude reaction is analyzed by $^1$H-NMR to reveal that the major part of the N—H groups of 2,2,6,6-tetramethylpiperidinic units of Chimassorb 966 are converted into the corresponding N-octyl thus forming compound (103).

Melting point: 125-195° C.

LCMS analysis provides the following product distribution in the final crude residue:

| Component | Approx. Amount (%) | Mass Found |
|---|---|---|
| Chimassorb 966 (starting material) | <5% | 1196 Not detected |
| Mono-substituted | ~10% | 1338 |
| Di-substituted | ~30% | 1423 |

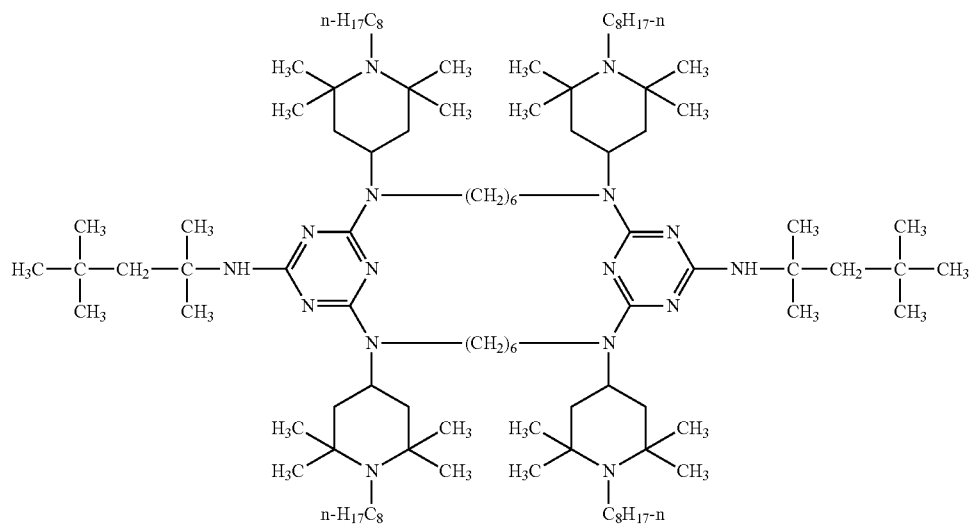

(103)

| Component | Approx. Amount (%) | Mass Found |
|---|---|---|
| Tri-substituted | ~45% | 1535 |
| Tetra-substituted | ~15% | 1648 |

EXAMPLE 4

Synthesis of Compound (104) Starting from Chimassorb 966

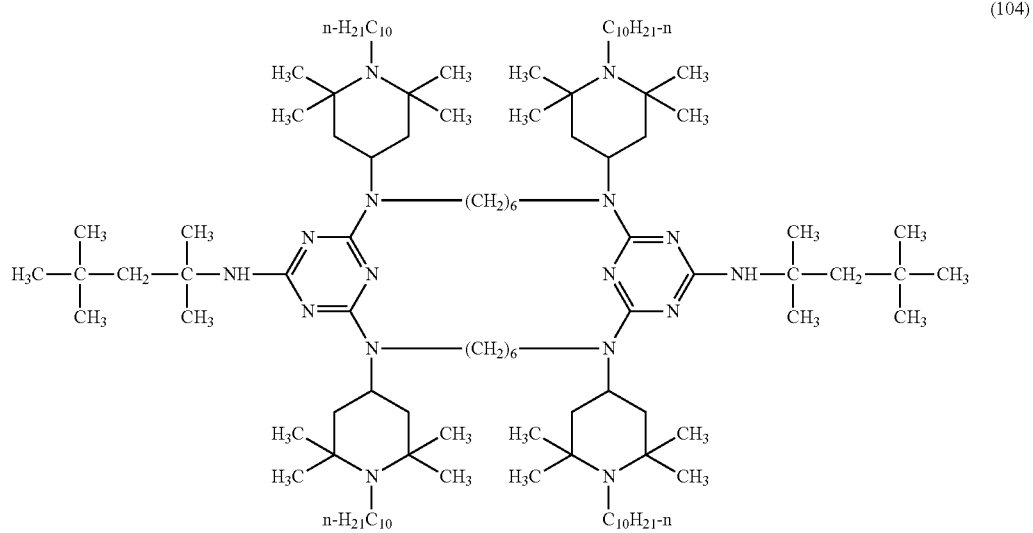

(104)

A four-necked round-bottom flask equipped with a mechanical stirrer, thermocouple, dropping funnel and condenser is successively charged with 50.0 g of Chimassorb 996, 200 ml of 1,2-dichlorobenzene, 23.0 g of potassium carbonate, 1.0 g of potassium iodide and 56.0 g of 1-bromo decane. The mixture is maintained under stirring for 10 hours at reflux temperature. Thus, 200 ml of water are added to the cooled reaction solution and the organic phase is then separated and concentrated under reduced pressure. The crude residue is analyzed by $^1$H-NMR to reveal that the major part of the N—H groups of 2,2,6,6-tetramethylpiperidinic units of Chimassorb 966 are converted into the corresponding N-decyl thus forming compound (104).

Melting point: 76-109° C.

LCMS analysis provides the following product distribution in the final crude residue:

| Component | Approx. Amount (%) | Mass Found |
| --- | --- | --- |
| Chimassorb 966 (starting material) | <5% | 1196 Not detected |
| Mono-substituted | ~10% | 1338 |
| Di-substituted | ~20% | 1478 |
| Tri-substituted | ~20% | 1619 |
| Tetra-substituted | ~15% | 1759 |

EXAMPLE 5

Synthesis of Compound 105 Starting from Chimassorb 966

A four-necked round-bottom flask equipped with a mechanical stirrer, thermocouple, dropping funnel and condenser is successively charged with 50.0 g of Chimassorb 996, 250 ml of 1,2-dichlorobenzene, 23.0 g of potassium carbonate, 1.0 g of potassium iodide and 63.0 g of 1-dodecyl bromide. The mixture is maintained under stirring for 35 hours at reflux temperature. Thus, the filtered solution is recrystallized with ethanol and exsiccated under reduced pressure. The $^1$H-NMR analysis of the obtained white precipitate reveals that the major part of the N—H groups of 2,2,6,6-tetramethylpiperidinic units of Chimassorb 966 are converted into the corresponding N-dodecyl thus forming compound 105.

Melting point: 126-152° C.

LCMS analysis provides the following product distribution in the final solid:

| Component | Approx. Amount (%) | Mass Found |
| --- | --- | --- |
| Chimassorb 966 (starting material) | ~10% | 1198 |
| Mono-substituted | ~20% | 1366 |
| Di-substituted | ~30% | 1535 |
| Tri-substituted | ~25% | 1702 |
| Tetra-substituted | ~10% | 1871 |

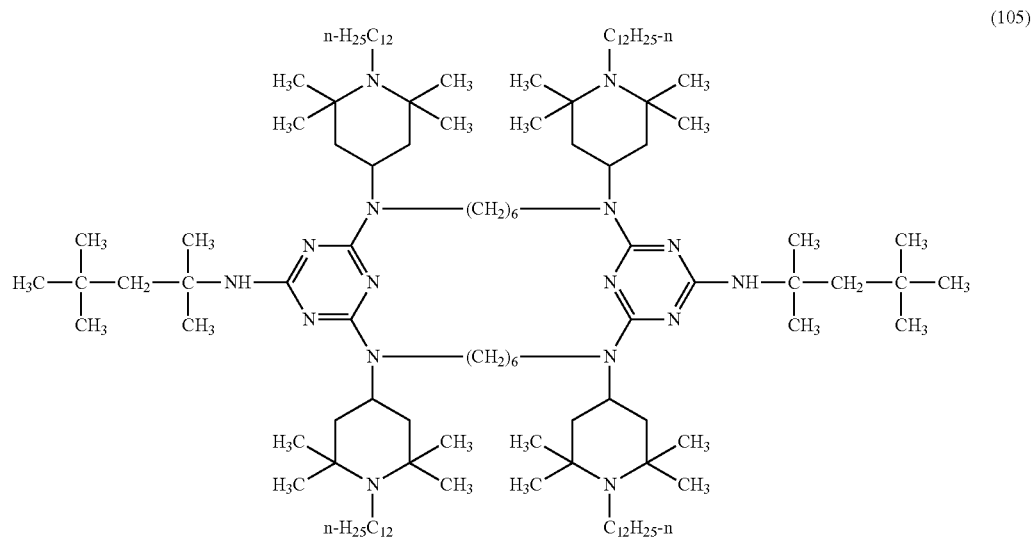

(105)

EXAMPLE 6

Synthesis of Compound (106) Starting from Compound A

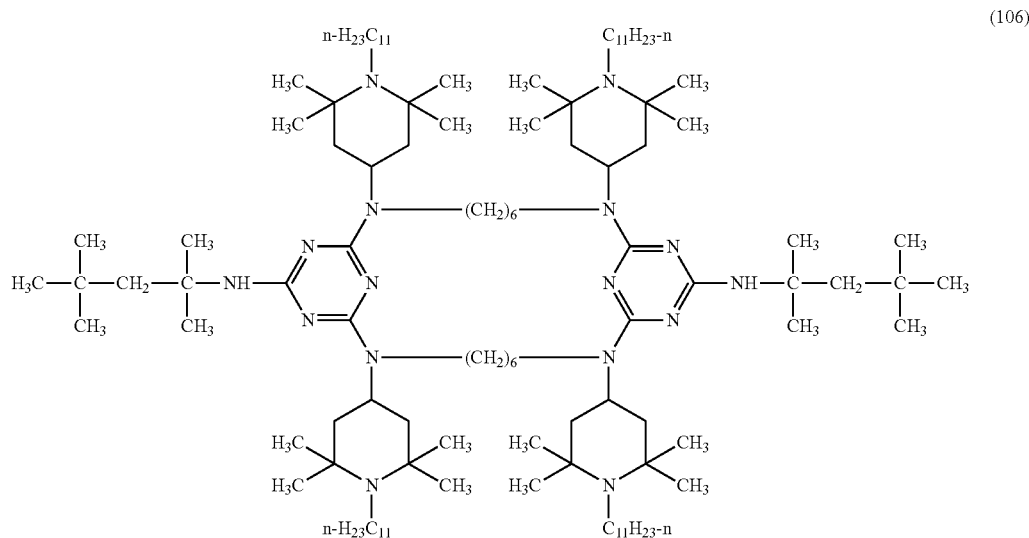

Synthesis of compound (A) starting from Chimassorb 966:

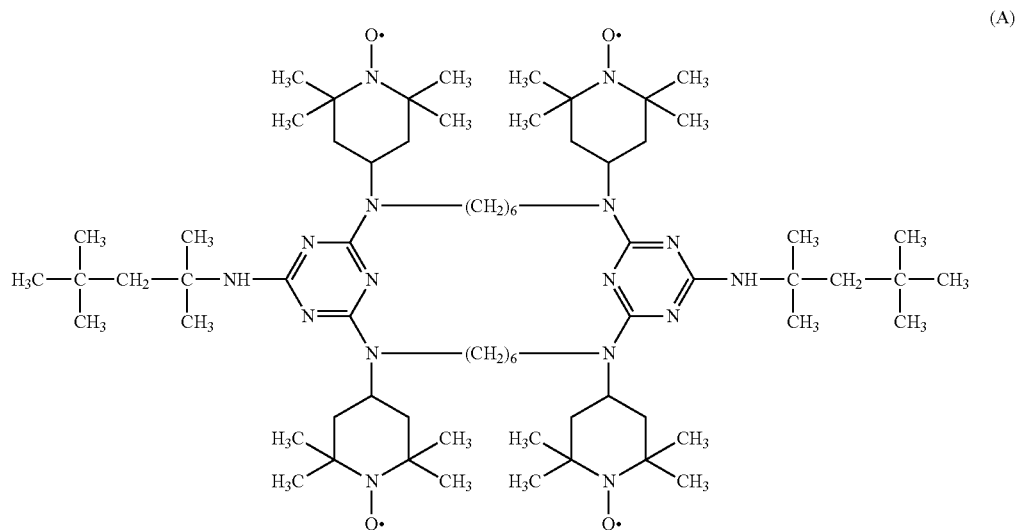

Compound A can be prepared according to the procedure reported in WO 2002058844 t or by means of state of the art oxidation procedures.

Synthesis of Compound (106):

A four-necked round-bottom flask equipped with a mechanical stirrer, thermocouple, dropping funnel and condenser is successively charged with 100.0 g of compound A, 500 ml of dichloromethane, 147.0 g of dodecyl aldehyde, 60.0 g of acetic acid and 3.0 g of copper(I) chloride. Thus, 80.0 g of 30% hydrogen peroxide solution in water are added dropwise to the stirred mixture maintaining the temperature less than 37° C. Then, the reaction is left to react 19 hours at 37° C. and after that 30% sodium hydroxide solution is added to the mixture until the pH of the water phase is 11. The organic phase is separated from the water phase, washed twice with water and concentrated under vacuum. The residue is washed with ethanol obtaining a slightly brown solid.

Melting point: 127-137° C.

LCMS analysis provides the following product distribution in the final solid:

| Component | Approx. Amount (%) | Mass Found |
|---|---|---|
| Chimassorb 966 (starting material) | ≦5% | 1196 not detected |
| Mono-substituted | ≦5% | 1368 |
| Di-substituted | ~20% | 1538 |
| Tri-substituted | ~35% | 1708 |
| Tetra-substituted | ~45% | 1878 |

I. Alternative Synthesis of Compound (106):

A four-necked round-bottom flask equipped with a mechanical stirrer, thermocouple, dropping funnel and condenser is successively charged with 30.0 g of compound B, 50 ml dichlororethane and 300 ml of chlorobenzene. 42.0 g of lauroyl peroxide dissolved in 100 ml dichloroethane are added dropwise to the stirred mixture over a period of 3 h at a temperature of 105° C. Stirring is continued for 8 h at the indicated temperature. The reaction mixture is concentrated in vacuo. 400 ml isopropanol is added and the mixture is heated to 75° C. While stirring at this temperature product started to precipitate. After 2 h the mixture is cooled to room temperature. The solid is collected by filtration and washed twice with cold isopropanol. Compound (106) is obtained as an off-white solid (23 g).

Melting point: 125-145° C.

II. Further Alternative Synthesis of Compound (106):

a) Preparation of α,α'-dihydroxydidodecyl peroxide 30.0 g dodecanal is dissolved in 45 ml tert.-butylmethyl ether. 36 g 30% hydrogen peroxide solution is added over a period of 15 minutes and the forming emulsion is stirred for 3 h at rt. The reaction mixture is extracted 5 times with 10 ml water and subsequently dried over sodium sulfate. The solvent is removed in vacuo to give the product as a white powder (20.9 g).

b) A four-necked round-bottom flask equipped with a mechanical stirrer, thermocouple, dropping funnel and condenser is successively charged with 3.0 g of compound A, 5 ml dichlororethane and 30 ml of chlorobenzene. 4.2 g of α,α'-dihydroxydidodecyl peroxide dissolved in 10 ml chlorobenzene are added dropwise to the stirred mixture over a period of 2 h at a temperature of 105° C. Stirring is continued for 8 h at the indicated temperature. The reaction mixture is concentrated in vacuo. 40 ml isopropanol is added and the mixture is heated to 75° C. While stirring at this temperature product starts to precipitate. After 3 h the micture is cooled to rt. The solid is collected by filtration and washed twice with cold isopropanol. Compound (6) is obtained as an off white solid (2.2 g).

Melting point: 124-145° C.

EXAMPLE 7

Synthesis of Compound (107) Starting from Compound A

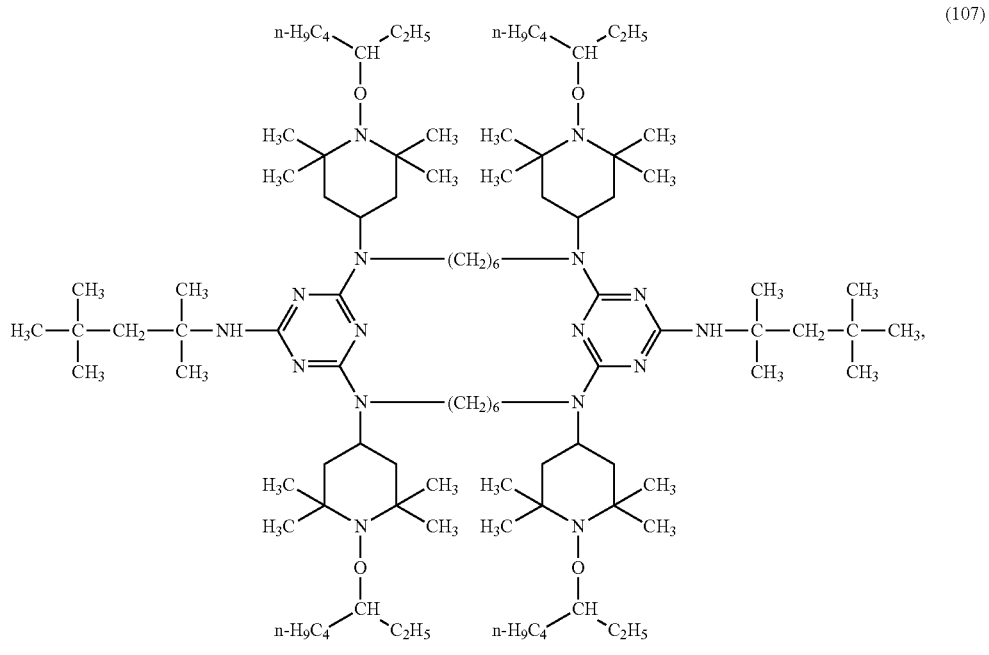

(107)

A four-necked round-bottom flask equipped with a mechanical stirrer, thermocouple, dropping funnel and condenser is successively charged with 50.0 g of compound A, 200 ml of dichloromethane, 73.5 g of 2-ethylcapronaldehyde, 30.0 g of acetic acid and 1.5 g of copper(I) chloride. Thus, 40.0 g of 30% hydrogen peroxide solution in water are added dropwise to the stirred mixture in 1 hour and 30 minutes maintaining the temperature less than 39° C. Then, the reaction is left to react 19 hours at 39° C. and after that 30% sodium hydroxide solution is added to the mixture until the pH of the water phase is 11. The organic phase is separated from the water phase, washed twice with water and concentrated under vacuum obtaining a white solid.

Melting point: 213-222° C.

LCMS analysis provides the following product distribution (%) in the final solid:

| Component | Approx. Amount (%) | Mass Found |
|---|---|---|
| Starting material | ≦5% | 1258 not detected |
| Mono-substituted | ~10% | 1357 |
| Di-substituted | ~20% | 1456 |
| Tri-substituted | 15-25% | 1556 |
| Tetra-substituted | 35-45% | 1655 |

EXAMPLE 8

Synthesis of Compound (108) Starting from Chimassorb 966 and Compound (B)

denser is successively charged with 50.0 g of Chimassorb 966, 500 ml of chloro-benzene, 109.0 g of compound (B), 34.5 g of potassium carbonate and 6.9 g of potassium iodide. The mixture is maintained under stirring for 16 hours at reflux temperature. Thus, water is added to the filtered solution and the organic phase is separated and concentrated under vacuum. The residue is washed with ethanol and subsequently with water. The formed precipitated is filtered and exsiccated in oven. The $^1$H-NMR analysis of the obtained precipitated reveals that the major part of the N—H groups of 2,2,6,6-tetramethylpiperidinic units of Chimassorb 966 are converted into the corresponding N-alkyl groups thus forming compound (108).

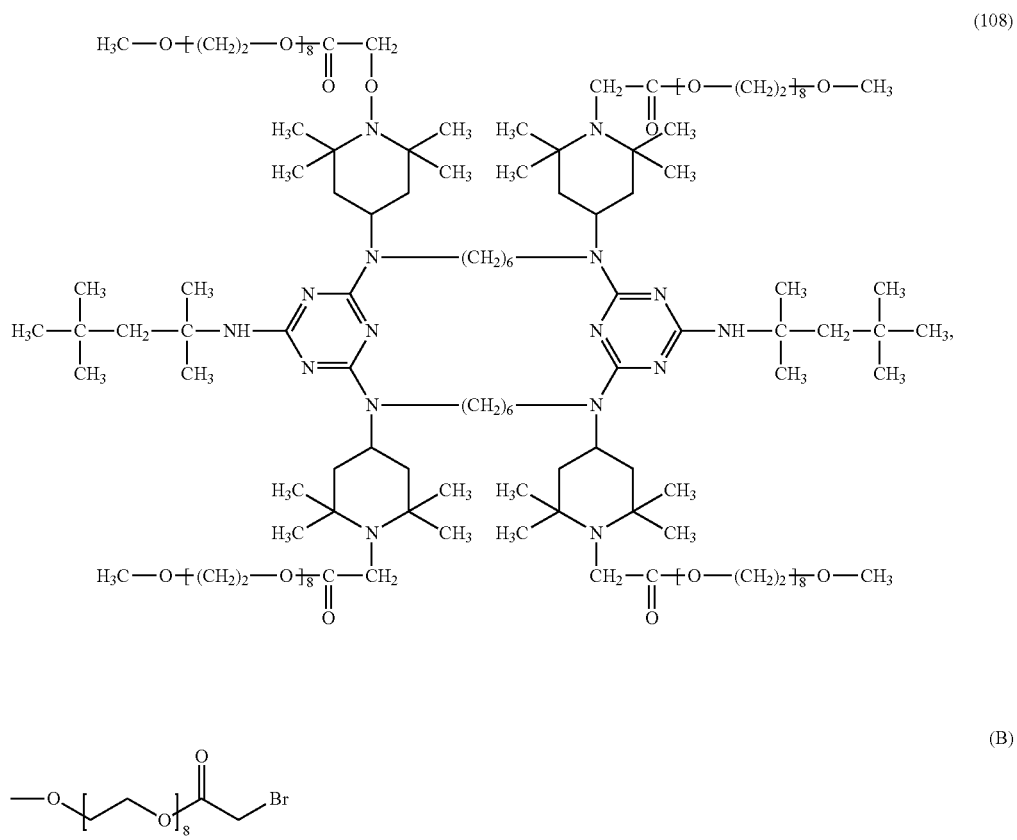

Synthesis of Compound (B):

A four-necked round-bottom flask equipped with a mechanical stirrer, thermocouple, dropping funnel and condenser is successively charged with 140.0 g of Poly(ethylene glycol) methyl ether (Mw=350), 133.6 g of ethyl bromoacetate, 2.0 g of p-toluenesulfonic acid monohydrate, 400 ml of xylene. The mixture is maintained under stirring for 16 hours at reflux temperature. Thus, the solution is concentrated under vacuum and filtered. The $^1$H-NMR analysis of the obtained liquid confirms the structure of the compound B.

Synthesis of Compound (108):

A four-necked round-bottom flask equipped with a mechanical stirrer, thermocouple, dropping funnel and con- Melting point: 128-140° C.

GPC-UV Chromatogram analysis provides the following product distribution:

| Component | Approx. Amount (%) | Mass Found |
|---|---|---|
| Starting material | ≦5% | 1215 not detected |
| Mono-substituted | ~25% | 1720 |
| Di-substituted | ~35% | 2010 |
| Tri-substituted | ~30% | 2364 |
| Tetra-substituted | ~10% | 2730 |

EXAMPLE 9

Alternative Synthesis of Compound (102) Starting from Compound (A)

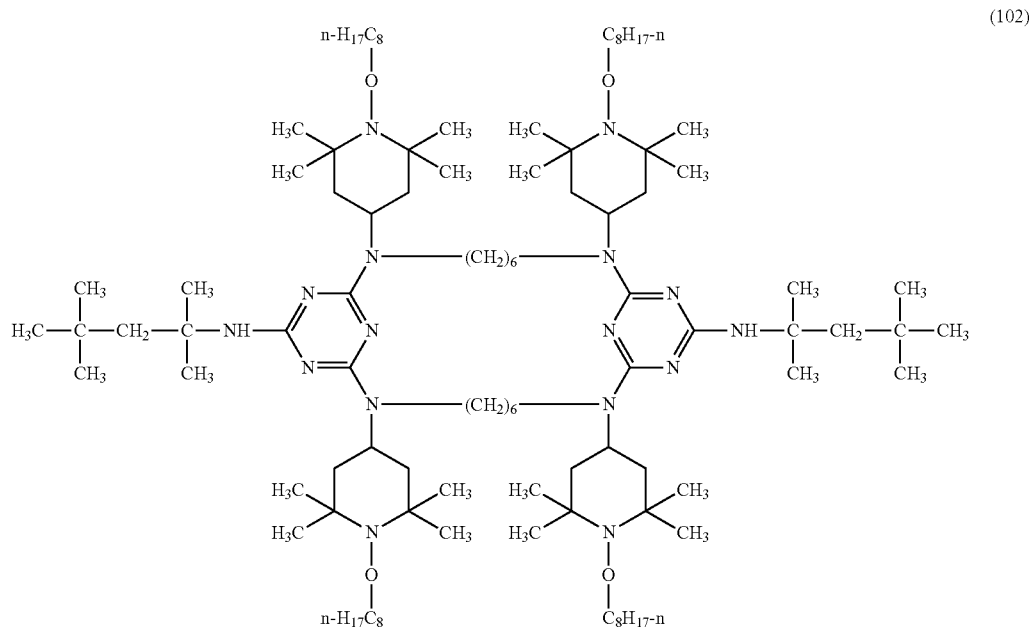

A four-necked round-bottom flask equipped with a mechanical stirrer, thermocouple, dropping funnel and condenser is successively charged with 3.0 g of compound A, 10 ml dichlororethane and 15 ml of chlorobenzene. 3.3 g of nonaoyl peroxide dissolved in 10 ml dichloroethane are added dropwise to the stirred mixture over a period of 1.5 h at a temperature of 105° C. Stirring is continued for 10 h at the indicated temperature. The reaction mixture is concentrated in vacuo. 40 ml isopropanol is added and the mixture is heated to 75° C. While stirring at this temperature the product starts to precipitate. After 2 h the mixture is cooled to room temperature. The solid is collected by filtration and washed twice with cold isopropanol. Compound (102) is obtained as an off-white solid (2.3 g).

Melting point: 162-169° C.
Application Data:
Film Manufacture:

In a turbo mixer (Caccia, Labo 10) additives are mixed with LDPE. The mixture is extruded at a maximum temperature of 200° C. using an O.M.C. twin-screw extruder (model ebv 19/25) to granules. The granules are subsequently mixed and diluted with the same LDPE in order to obtain the final composition for preparing a 150 μm thick film, using a blow-extruder (Dolci®) working at a maximum temperature of 210° C. The final concentrations of the LDPE films are indicated in Table 1.

TABLE 1

Final composition of the LDPE films

| Ref. | Additives |
|---|---|
| Film 1 | none |
| Film 2 | 0.4% Chimassorb 966 (commercial product as reference) |

TABLE 1-continued

Final composition of the LDPE films

| Ref. | Additives |
|---|---|
| Film 3 | 0.4% compound (106) |
| Film 4 | 0.4% compound (105) |
| Film 5 | 0.4% compound (107) |
| Film 6 | 0.4% Tinuvin NOR 371 (commercial product as reference) |
| Film 7 | 0.4% Chimassorb 119 (commercial product as reference) |
| Film 8 | 0.4% Adeka Stab LA 81 |

Gel Countings:

N° gels/m2 in the additivated LDPE films is counted with Film Scan FS3, sold by OCS Optical Control System. Results are reported in Table 2.

TABLE 2 n° gels/m² on additivated LDPE films

| Film | <400 μm | 400-800 μm | 800-1200 μm | >1200 μm | Sum |
|---|---|---|---|---|---|
| Film 1 | 79 | 10 | 2 | 0 | 91 |
| Film 2 | 1505 | 80 | 1.4 | 0 | 1586 |
| Film 3 | 334 | 35 | 2 | 0 | 371 |
| Film 4 | 371 | 57 | 3 | 0 | 431 |
| Film 5 | 317 | 39 | 2 | 1 | 359 |
| Film 6 | 418 | 25 | 1 | 0 | 445 |

Performances of Additives as Stabilizers in LDPE Films:
Light Exposure:

LDPE films are exposed in an ATLAS Weatherometer (model Ci65A) equipped with a 6500 W Xenon lamp (0.35 W/m²; continuous light cycle, black panel temperature=63° C.).

Evaluation Parameters:

1) Carbonyl Increment: Evaluation of the carbonyl band increment (1710 cm-1) in LDPE films additivated at 0.4% with compound are under applicative tests to assess the performances as light/heat stabilizers.

Stabilizer Performances of compounds 105 and 107 are depicted in the Tables 3 to 6.

TABLE 3

Carbonyl Increment of 150 μm additivated LDPE films upon WOM exposure

| Film | Time of exposure (h) | | | | | |
|---|---|---|---|---|---|---|
| | 0 | 540 | 1010 | 1530 | 3070 | 5130 |
| Film 6 (0.4% Tinuvin NOR 371) | 0.000 | 0.010 | 0.022 | 0.032 | 0.059 | 0.114 |
| Film 5 (0.4% compound 107) | 0.000 | 0.006 | 0.017 | 0.032 | 0.059 | 0.108 |

TABLE 4

Elongation % at break of 150 μm additivated LDPE films upon WOM exposure
Time of exposure (h)

| Film | 0 | 1030 | 1765 | 3060 | 4380 |
|---|---|---|---|---|---|
| Film 6 (0.4% Tinuvin NOR 371) | 100 | 92 | 91 | 77 | 66 |
| Film 5 (0.4% compound 107) | 100 | 100 | 88 | 88 | 65 |

TABLE 5

Carbonyl Increment of 150 μm additivated LDPE films upon WOM exposure
Time of exposure (h)

| Film | 0 | 1091 | 2225 | 2910 | 3760 | 5110 |
|---|---|---|---|---|---|---|
| Film 6 (0.4% Tinuvin NOR 371) | 0.000 | 0.016 | 0.026 | 0.033 | 0.043 | 0.051 |
| Film 7 (0.4% CHIMASSORB 119) | 0.000 | 0.007 | 0.025 | 0.029 | 0.037 | 0.049 |
| Film 4 (0.4% compound 105) | 0.000 | 0.007 | 0.019 | 0.023 | 0.033 | 0.039 |
| Film 8 (0.4% ADK STAB LA 81) | 0.000 | 0.019 | 0.024 | 0.027 | 0.033 | 0.037 |

TABLE 6

Elongation % at break of 150 μm additivated LDPE films upon WOM exposure
Time of exposure (h)

| Film | 0 | 1650 | 3335 | 5110 | 36955 |
|---|---|---|---|---|---|
| Film 6 (0.4% Tinuvin NOR 371) | 100 | 99 | 99 | 86 | 75 |
| Film 7 (0.4% CHIMASSORB 119) | 100 | 96 | 93 | 93 | 55 |
| Film 4 (0.4% compound 105) | 100 | 95 | 95 | 87 | 74 |
| Film 8 (0.4% ADK STAB LA 81) | 100 | 94 | 94 | 88 | 80 |

Performances as Flame Retardants in PP Films:

Processing and Flame Testing:

Unless stated otherwise, commercial polypropylene (MOPLEN HF500N, manufacturer: Basell) is extruded on a co-rotating twin-screw extruder ZSK25 from Coperion Werner & Pfleiderer at a temperature of Tmax=230° C. (heating zones 1-6), a throughput rate of 4 kg/h and 100 rpm under addition of basic-level stabilization (0.3% IRGANOX B225+ 0.05% Ca-stearate, IRGANOX B225 is a 1:1 mixture of IRGAFOS168 and IRGANOX 1010) and the additives indicated in Tables 1-2. After cooling in a water bath the polymer strand is granulated.

Test specimens are prepared by compression molding in a hot press (films thickness=200 μm, 250×110 mm, Fontjne TP200, pmax=50 kN, 230° C.).

The test samples are investigated for flame retardancy in accordance to DIN 4102-B2 (edge ignition, flame length=40 mm).

TABLE 1

(flaming test on 200 μm pressed films according to DIN 4102-B2, edge ignition, 40 mm flame, data ex PDR100388)

| Example | Additives | Weight loss/% | Burn length/mm | Burning drips | Pass/Fail |
|---|---|---|---|---|---|
| Comparison 1 | w/o | 100 | 190 | yes | Fail |
| Inventive 1 | 0.50% compound 106 | 3.8 | 100 | no | Pass |
| Inventive 2 | 0.50% compound 107 | 6.9 | 102 | yes | Pass |

Low values for weight loss and burn length reflect increased flame retardancy. Another remarkable aspect which reflects the excellent FR behavior is the non-burning dripping.

The invention claimed is:

1. A composition comprising (a) a natural or synthetic polymer subject to degradation induced by light, heat or oxidation, and (b) 0.001 to 10% by weight, relative to the weight of the natural or synthetic polymer, of a product mixture containing components b-I, b-II, b-III and b-IV;

component b-I being a compound of formula (I) with a degree of substitution of 1 in an amount of from 5 to 25 parts by weight, component b-II being a compound of formula (I) with a degree of substitution of 2 in an amount of from 5 to 35 parts by weight, component b-III being a compound of formula (I) with a degree of substitution of 3 in an amount of from 10 to 45 parts by weight and component b-IV being a compound of formula (I) with a degree of substitution of 4 in an amount of from 10 to 45 parts by weight, the sum of the parts of components bI to bIV being 100;

formula (I) being

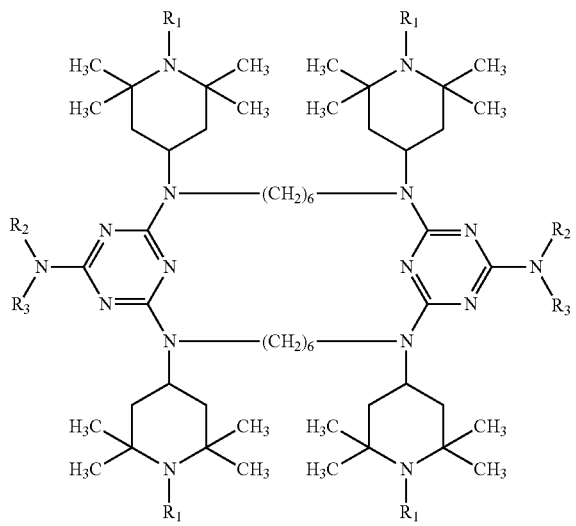

wherein
the radicals $R_1$ are $C_4$-$C_{20}$alkyl, $C_4$-$C_{20}$alkoxy, $C_3$-$C_{12}$cycloalkoxy or a group

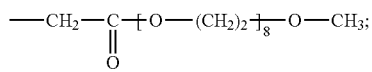

wherein for component b-I, b-II and b-III the radicals $R_1$ can additionally be hydrogen, oxygen or hydroxyl;
where degree of substitution denotes the number of substituents $R_1$ which are $C_4$-$C_{20}$alkyl, $C_4$-$C_{20}$alkoxy, $C_3$-$C_{12}$cycloalkoxy or a group

—CH$_2$—C(=O)—(O—(CH$_2$)$_2$)$_8$—O—CH$_3$;

and
the radicals $R_2$ and $R_3$ are independently of one another hydrogen, $C_1$-$C_{12}$alkyl, $C_5$-$C_{12}$cycloalkyl unsubstituted or substituted by 1 to 3 $C_1$-$C_4$alkyl; phenyl unsubstituted or substituted by 1 to 3 radicals selected from —OH and $C_1$-$C_{10}$alkyl; $C_7$-$C_9$phenylalkyl unsubstituted or substituted on the phenyl by 1 to 3 radicals selected from —OH and
$C_1$-$C_{10}$alkyl; or a group of formula (I-1)

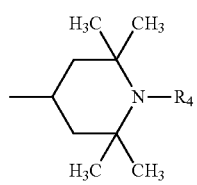

wherein $R_4$ is hydrogen, $C_4$-$C_{20}$alkyl, $C_4$-$C_{20}$alkoxy, $C_3$-$C_{12}$cycloalkoxy or a group of formula

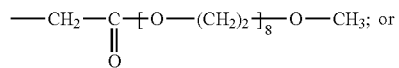

the radicals $R_2$ and $R_3$, together with the nitrogen they are attached to, form a morpholino group.

2. A composition according to claim 1 wherein the $R_1$ are $C_4$-$C_{12}$alkyl, $C_4$-$C_{12}$alkoxy or $C_5$-$C_6$cycloalkoxy.

3. A composition according to claim 1 wherein —NR$_2$R$_3$ is a group of formulae (II)

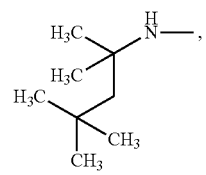

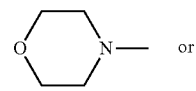

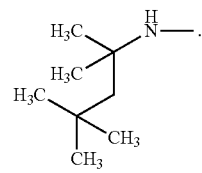

4. A composition according to claim 1 wherein —NR$_2$R$_3$ is of formula (II)

5. A composition according to claim 1 wherein the natural or synthetic polymer is a polyolefin.

6. A compound of formula (Ia)

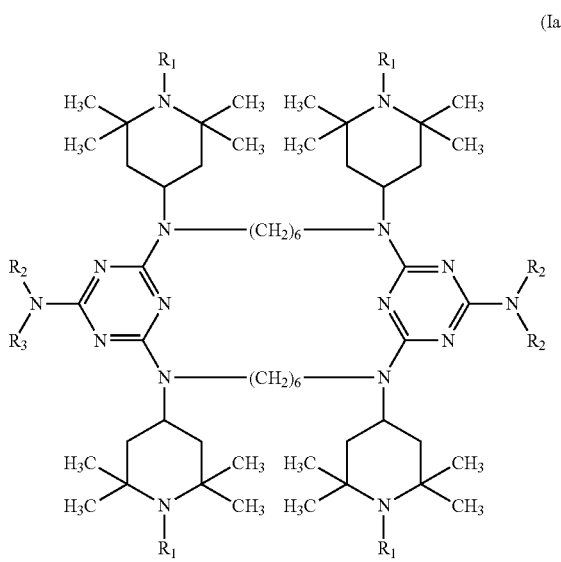

wherein
2, 3 or 4 of the radicals $R_1$ are $C_4$-$C_{20}$alkoxy, $C_3$-$C_{12}$cycloalkoxy or a group

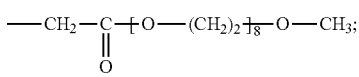

and the remaining radicals $R_1$ are hydrogen, oxygen or hydroxyl; and the radicals $R_2$ and $R_3$ are independently of one another hydrogen, $C_1$-$C_{12}$alkyl, $C_5$-$C_{12}$cycloalkyl unsubstituted or substituted by 1 to 3 $C_1$-$C_4$alkyl; phenyl unsubstituted or substituted by 1 to 3 radicals selected from —OH and $C_1$-$C_{10}$alkyl; $C_7$-$C_9$phenylalkyl unsubstituted or substituted on the phenyl by 1 to 3 radicals selected from —OH and $C_1$-$C_{10}$alkyl; or a group of formula (I-1)

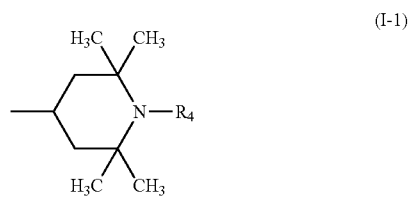

wherein $R_4$ is hydrogen, $C_4$-$C_{20}$alkyl, $C_4$-$C_{20}$alkoxy, $C_3$-$C_{12}$cycloalkoxy or a group

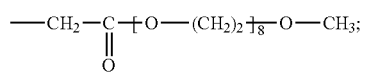

or the radicals $R_2$ and $R_3$, together with the nitrogen they are attached to, form a morpholino group.

7. A compound according to claim 6 selected from 1, 2, 6, 7 and 8

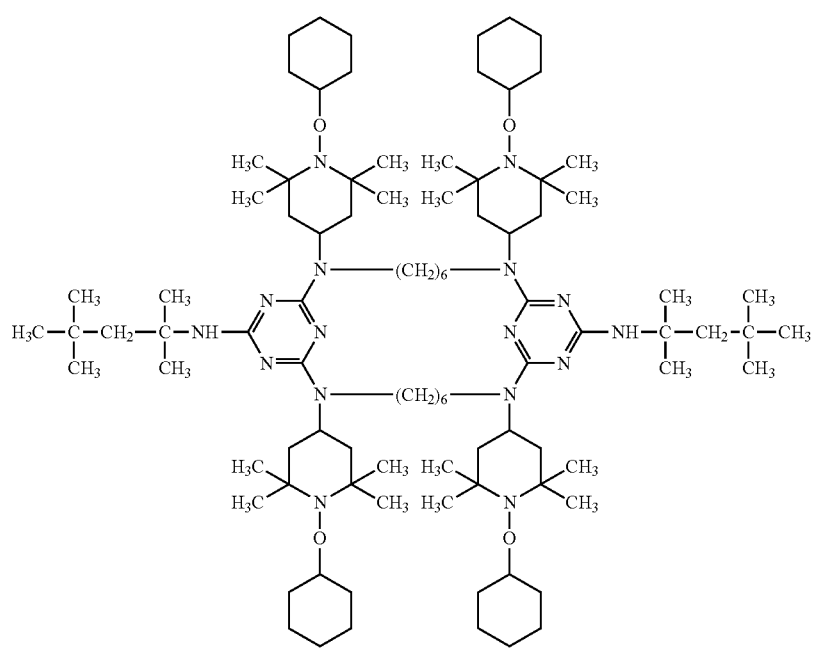

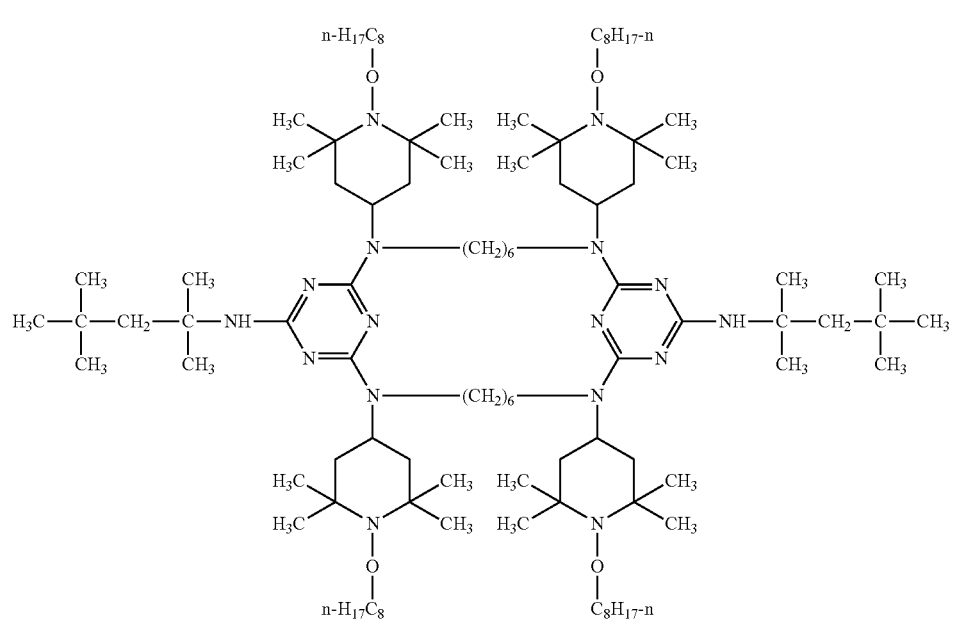
(2)
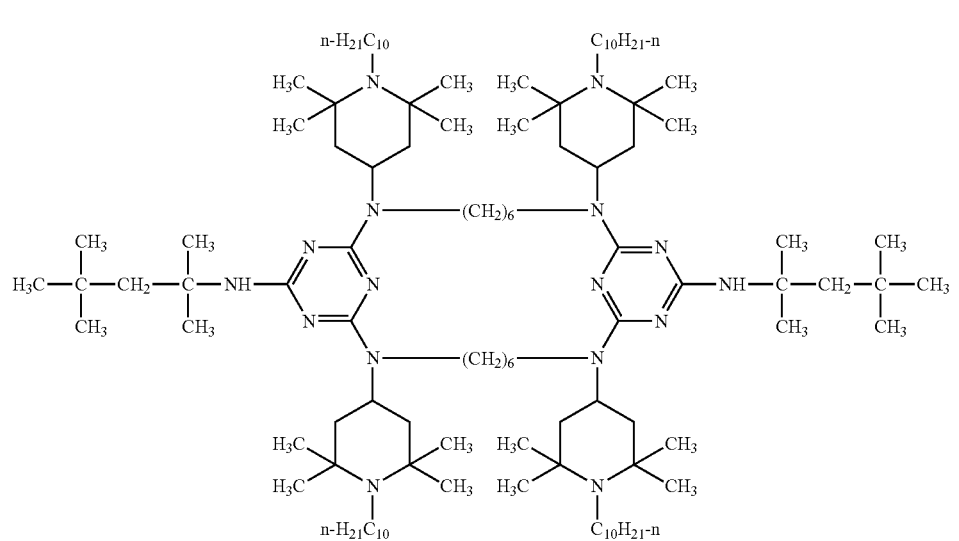
(4)
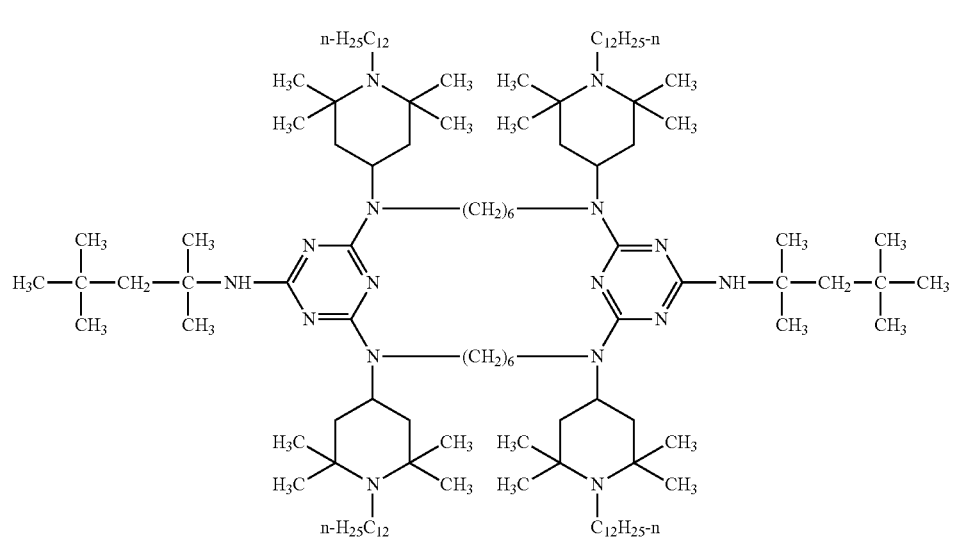
(5)

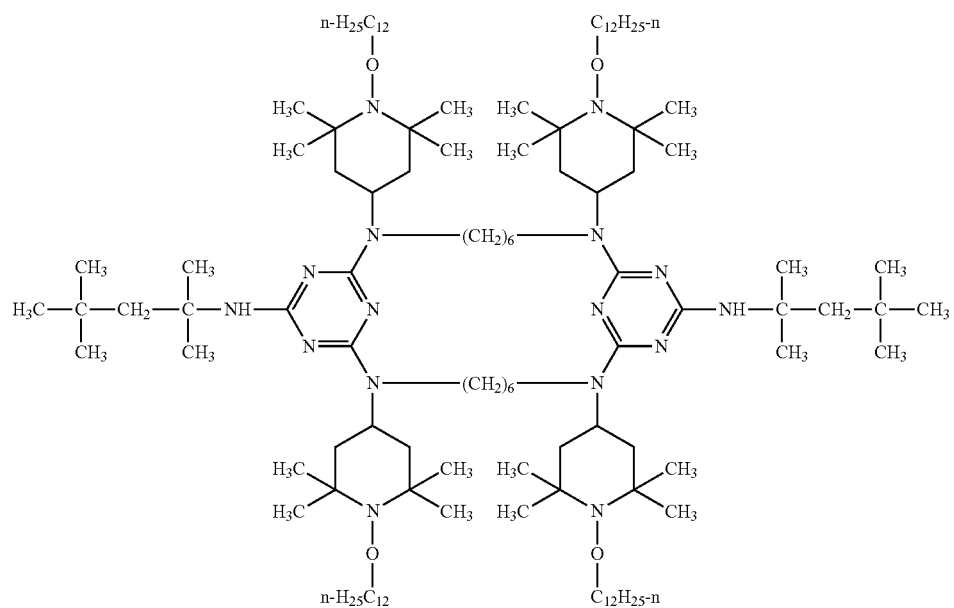
(6)
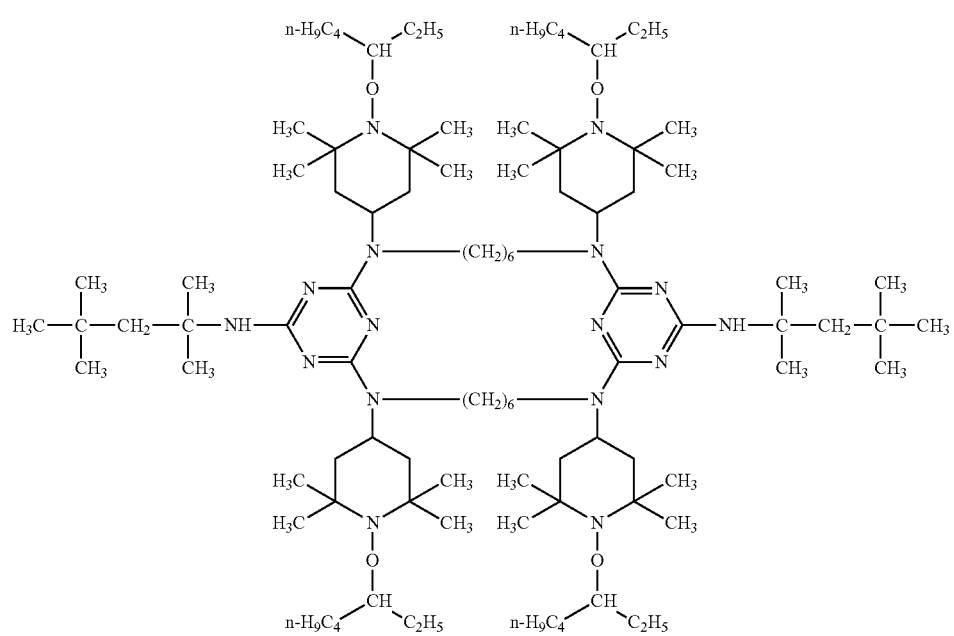
(7)

-continued (8)

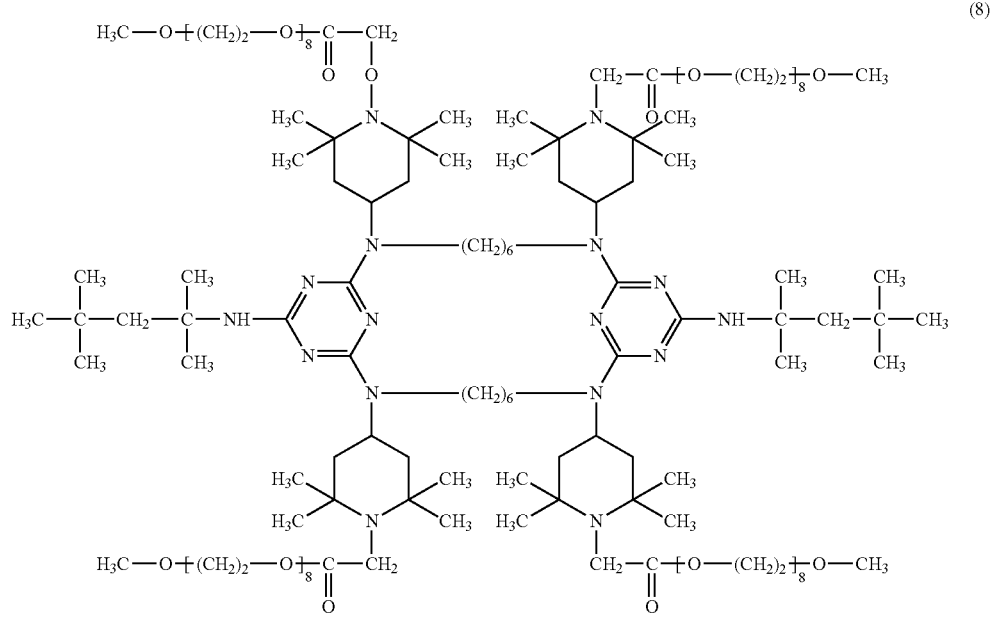

8. A composition comprising a product mixture containing components b-I, b-II, b-III and b-IV;

component b-I being a compound of formula (I) with a degree of substitution of 1 in an amount of from 5 to 25 parts by weight, component b-II being a compound of formula (I) with a degree of substitution of 2 in an amount of from 5 to 35 parts by weight, component b-III being a compound of formula (I) with a degree of substitution of 3 in an amount of from 10 to 45 parts by weight and component b-IV being a compound of formula (I) with a degree of substitution of 4 in an amount of from 10 to 45 parts by weight, the sum of the parts of components bI to bIV being 100;

formula (I) being (I)

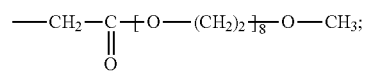

wherein the radicals $R_1$ are $C_4$-$C_{20}$alkyl, $C_4$-$C_{20}$alkoxy, $C_3$-$C_{12}$cycloalkoxy or a group

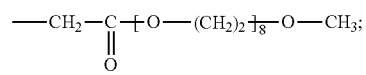

wherein for component b-I, b-II and b-III the radicals $R_1$ can additionally be hydrogen, oxygen or hydroxyl;

where degree of substitution denotes the number of substituents $R_1$ which are $C_4$-$C_{20}$alkyl, $C_4$-$C_{20}$alkoxy, $C_3$-$C_{12}$cycloalkoxy or a group

—CH$_2$—C(=O)—O—(CH$_2$)$_2$—]$_8$—O—CH$_3$;

and the radicals $R_2$ and $R_3$ are independently of one another hydrogen, $C_1$-$C_{12}$alkyl, $C_5$-$C_{12}$cycloalkyl unsubstituted or substituted by 1 to 3 $C_1$-$C_4$alkyl; phenyl unsubstituted or substituted by 1 to 3 radicals selected from —OH and $C_1$-$C_{10}$alkyl; $C_7$-$C_9$phenylalkyl unsubstituted or substituted on the phenyl by 1 to 3 radicals selected from —OH and $C_1$-$C_{10}$alkyl; or a group of formula (I-1)

(I-1)

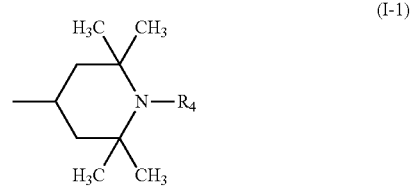

wherein R$_4$ is hydrogen, C$_4$-C$_{20}$alkyl, C$_4$-C$_{20}$alkoxy, C$_3$-C$_{12}$cycloalkoxy or a group

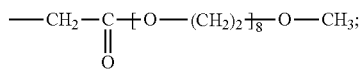

the radicals R$_2$ and R$_3$, together with the nitrogen they are attached to, form a morpholino group.

9. A process for the stabilization of a natural or synthetic polymer subject to degradation induced by light, heat or oxidation comprising incorporating into said polymer 0.001 to 10% by weight, relative to the weight of the natural or synthetic polymer, of a composition according to claim 8.

10. An agricultural article made of (a) a natural or synthetic polymer subject to degradation induced by light, heat or oxidation, and (b) 0.001 to 10% by weight, relative to the weight of the natural or synthetic polymer, of a product mixture containing components b-I, b-II, b-III and b-IV;

component b-I being a compound of formula (I) with a degree of substitution of 1 in an amount of from 5 to 25 parts by weight, component b-II being a compound of formula (I) with a degree of substitution of 2 in an amount of from 5 to 35 parts by weight, component b-III being a compound of formula (I) with a degree of substitution of 3 in an amount of from 10 to 45 parts by weight and component b-IV being a compound of formula (I) with a degree of substitution of 4 in an amount of from 10 to 45 parts by weight, the sum of the parts of components bI to bIV being 100;

formula (I) being

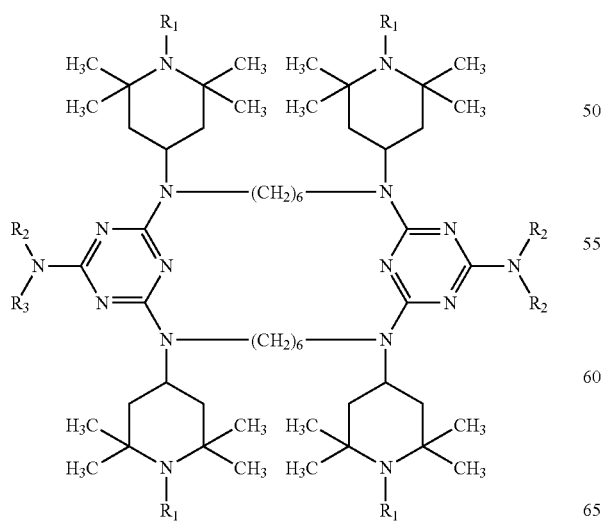

wherein the radicals R$_1$ are C$_4$-C$_{20}$alkyl, C$_4$-C$_{20}$alkoxy, C$_3$-C$_{12}$cycloalkoxy or a group

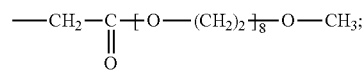

wherein for component b-I, b-II and b-III the radicals R$_1$ can additionally be hydrogen, oxygen or hydroxyl;

where degree of substitution denotes the number of substituents R$_1$ which are C$_4$-C$_{20}$alkyl, C$_4$-C$_{20}$alkoxy, C$_3$-C$_{12}$cycloalkoxy or a group

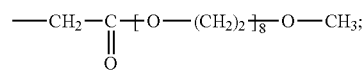

and the radicals R$_2$ and R$_3$ are independently of one another hydrogen, C$_1$-C$_{12}$alkyl, C$_5$-C$_{12}$cycloalkyl unsubstituted or substituted by 1 to 3 C$_1$-C$_4$alkyl; phenyl unsubstituted or substituted by 1 to 3 radicals selected from —OH and C$_1$-C$_{10}$alkyl; C$_7$-C$_9$phenylalkyl unsubstituted or substituted on the phenyl by 1 to 3 radicals selected from —OH and C$_1$-C$_{10}$alkyl; or a group of formula (I-1)

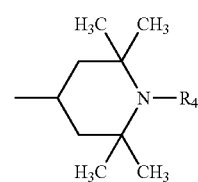

wherein R$_4$ is hydrogen, C$_4$-C$_{20}$alkyl, C$_4$-C$_{20}$alkoxy, C$_3$-C$_{12}$cycloalkoxy or a group

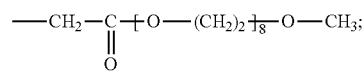

or the radicals R$_2$ and R$_3$, together with the nitrogen they are attached to, form a morpholino group.

11. An agricultural article according to claim 10 wherein the compounds of formula (I) are of formula (Ic)

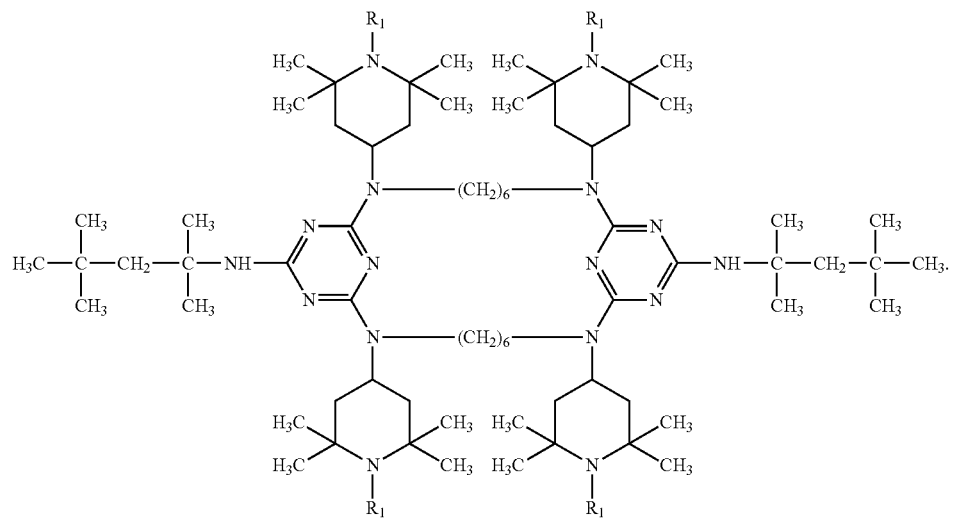
* * * * *